United States Patent
Teshima

(10) Patent No.: US 6,272,470 B1
(45) Date of Patent: Aug. 7, 2001

(54) ELECTRONIC CLINICAL RECORDING SYSTEM

(75) Inventor: Fumiaki Teshima, Nishinasuno-machi (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 08/922,458

(22) Filed: Sep. 3, 1997

(30) Foreign Application Priority Data

Sep. 3, 1996 (JP) .................................................. 8-233295

(51) Int. Cl.[7] ........................................................ G06F 17/60
(52) U.S. Cl. ............................................. 705/3; 705/2
(58) Field of Search ............................ 705/2, 3, 17, 21, 705/26, 42, 41, 43; 235/375, 487; 707/513

(56) References Cited

U.S. PATENT DOCUMENTS

| | | | |
|---|---|---|---|
| 4,228,506 | * 10/1980 | Ripley et al. | 705/3 |
| 4,988,855 | * 1/1991 | Iijima | 235/492 |
| 5,291,399 | * 3/1994 | Chaco | 364/413.02 |

(List continued on next page.)

FOREIGN PATENT DOCUMENTS

| | | | |
|---|---|---|---|
| 57-36491A | * | 2/1982 | (JP) . |
| 6-215030A | * | 8/1994 | (JP) . |
| 6-325056 | * | 11/1994 | (JP) . |
| 7-141112A | * | 6/1995 | (JP) . |
| 7-311807 | | 11/1995 | (JP) . |
| 8-137758 | * | 5/1996 | (JP) . |
| WO 87/02160 | * | 4/1987 | (WO) . |

OTHER PUBLICATIONS

Anon., "Multiple Caching Schemes in a Lan–Attached Server," IBM Technical Disclosure Bulletin, vol. 38, No. 4, pp. 143–145, Apr. 1995.*

Comeau, L.W., "Portable Personal Medical History File," IBM Technical Disclosure Bulletin, vol. 19, No. 20, pp. 4800–4801, May 1977.*

Kindel, S., "Smart Cards," Financial World, vol. 162, No. 2, p. 47, Jan. 1993.*

Syedain, H., "Making the Smart Move," Marketing, p. 16, Feb. 1993.*

Gruberman, K., "DiskFit Direct; DiskFit Pro," MacUser, vol. 9, No. 8, p. 79, Aug. 1993.*

Daniele, E., "Is Smarter Better," Insurance & Technology, vol. 20, No. 10, pp. 46–54, Oct. 1995.*

Ziegler, J., "Health Care's Search for an Information Injection," Business & Health, vol. 14, No. 4, pp.33–38, Apr. 1996.*

Anon., "Germany: Brokat Develops Encryption for Internet," Electronic Payments International, No. 111, p. 3, Sep. 1996.*

*Primary Examiner*—Vincent Millin
*Assistant Examiner*—Nicholas David Rosen
(74) *Attorney, Agent, or Firm*—Oblon, Spivak, McClelland, Maier & Neustadt, P.C.

(57) ABSTRACT

There is provided an electronic clinical recording system handling, as electronic data, information including a patient's consultation record. The system comprises a portable storage medium for storing the patient's consultation record; an element for writing the patient's consultation record described in a structured language into the storage medium; and an element for reading the patient's consultation record from the storage medium. The writing element includes a converting/producing element for converting or producing link information in the consultation record when the consultation record is written in the storage medium, the link information being indicative of making reference to one or more specified files relevant to the consultation record and prepared as external information. The reading element includes a data acquiring/referencing element for acquiring or referencing the one or more specified files indicated by the link information when the consultation record is read from the storage medium.

22 Claims, 14 Drawing Sheets

U.S. PATENT DOCUMENTS

| | | | | |
|---|---|---|---|---|
| 5,297,249 | * | 3/1994 | Bernstein et al. | 345/356 |
| 5,319,543 | * | 6/1994 | Wilhelm | 705/3 |
| 5,339,400 | * | 8/1994 | Iijima | 711/115 |
| 5,499,293 | * | 3/1996 | Behram et al. | 380/4 |
| 5,542,087 | * | 7/1996 | Neimat et al. | 707/10 |
| 5,594,637 | * | 1/1997 | Eisenberg et al. | 705/2 |
| 5,644,778 | * | 7/1997 | Burkes et al. | 395/800 |
| 5,675,493 | * | 10/1997 | Schwartz et al. | 364/464.03 |
| 5,799,212 | * | 8/1998 | Ohmori | 710/73 |
| 5,832,447 | * | 11/1998 | Rieker et al. | 705/2 |
| 5,832,450 | * | 11/1998 | Myers et al. | 705/3 |
| 5,842,211 | * | 11/1998 | Horadan et al. | 707/10 |
| 5,867,821 | * | 2/1999 | Ballantyne et al. | 705/2 |
| 5,874,954 | * | 2/1999 | Kilmer et al. | 345/333 |
| 5,899,998 | * | 5/1999 | McGauley et al. | 707/104 |
| 5,922,045 | * | 7/1999 | Hanson | 709/206 |
| 5,924,074 | * | 7/1999 | Evans | 705/3 |
| 5,974,124 | * | 10/1999 | Schlueter, Jr. et al. | 379/106.02 |
| 6,018,748 | * | 1/2000 | Smith | 707/501 |
| 6,098,082 | * | 8/2000 | Gibbon et al. | 707/501 |
| 6,151,609 | * | 11/2000 | Truong | 707/505 |
| 6,157,914 | * | 12/2000 | Seto et al. | 705/3 |

* cited by examiner

ELECTRONIC CLINICAL RECORDING SYSTEM

BACKGROUND OF THE INVENTION

1. Field of the Invention

The present invention relates to a medical information system utilizing a portable storage unit represented by an IC card as a health care, medical care, or welfare card.

2. Description of the Related Art

Examples of utilizing a card type storage medium for a medical information system will be described below.

[1] An example of introducing an IC card to the field of health care, medical care, and welfare is an experimental project involving several local municipalities. In this example, a name, an address, a health insurance card number, a blood type, a history of side effects of medicines the person has suffered, allergies, information of medications, and information of examinations, and others are stored in the IC card and utilized for health care consultation, vaccination, mass screening, and so on. Similar attempts have been made by several other municipalities. In the case of a certain municipality, the results of examinations and physical checkups, data of administered medicines, and information of a name and blood type were stored in the IC card, and used for diagnosis at a medical institution unconnected online or used in case of an unexpected accident. In this example, the role of the IC card is supplemental. A health care center, hospitals, and clinics are interconnected on an online network in order to share data of examinations and physical checkups. In another municipality, basic information such as a name and address of an individual as well as data of physical checkups, body conditions, and use frequencies of welfare facilities are stored in the IC card. Another example is an experiment on an IC card system having the capability of a health insurance card.

[2] As an example of utilizing an optical card, a system for recording the contents of a pocket book for the mother and baby, displaying graphically and successively the weight of a pregnant woman, an amount of uric protein, the length of the funds of the uterus, the lateral diameter of the fetal head, and the development curve concerning the fetal femur, all of which assist in readily grasping the conditions of the pregnant woman and the growth of the fetus, have been developed. In the case of this system, when the weight of a pregnant woman increases too much or trouble in a fetal growth pattern is detected, a color on a screen changes to attract attention.

From the viewpoint of a picture archiving and communication system (PACS), techniques described below are used to transmit medical images.

[3] PACS is a comprehensive medical-image management system to be implemented in a hospital for storing, retrieving, transmitting, and displaying medical images. An object of PACS is to improve the efficiency and quality of medical cares by electronically storing medical images. For transmitting medical images, a standard protocol for transmitting a medical image, Digital Imaging and Communication in Medicine (DICOM), has been widely used. Moreover, there is a method of recording medical images on an offline medium (magneto-optical disk) according to a format defined for electronically storing medical images, Image Save and Carry (IS&C), and of thus making it possible to carry the medical images. It is a teleradiology system that results from expansion of the application range of PACS for realizing local or remote medical care. According to the teleradiology system, public switched lines or the integrated services digital network (ISDN) is used to transmit information of medical images and to ask a specialist to send back the results of diagnosis. Thus, urgent diagnosis can be made properly and a treatment can be provided quickly.

Typical techniques for mutually utilizing medical data among hospitals will be described below.

[4] A plurality of specified hospitals are interconnected over telephone lines to form a system for managing medical information of all patients and information as to medical images in a centralized manner. Within the system, medical information of a patient can be referenced at any hospital.

[5] Medical information and information of medical images are stored in the form of a database at each hospital. The structured query language (SQL) is used to reference a database at another hospital. However, some databases may contain a few grammatical errors, or the relatively strict relationship between a client and server may bind referencing. Moreover, restrictions may be imposed on mere exchange of files other than database referencing in terms of diverse file formats or different operating systems (OSs).

By the way, the techniques described below are available from the viewpoint of an electronic clinical recording system.

[6] In an electronic clinical recording system under development in a certain university, electronic clinical recordings are expressed using E language such as the standard generalized markup language (SGML) or hyper text markup language (HTML), and managed as a medical database in a centralized manner. The organization of the World Wide Web (WWW) is used to realize retrieval and display. In this example, the electronic clinical recordings are regarded as structured statements, and the structures and broad units of meaning are indicated with tags.

An existing medical information system requests to satisfy the precondition that clinical recordings be managed in a centralized manner within each hospital. Medical information is cross-referenced under the precondition. This method has the following problems.

<1> A protocol adopted for information transmission is used on an inflexible standardized basis. It is hard to add an another entry item to a clinical recording.

<2> It is time-consuming to search for necessary information from enormous information. Since the work of retrieval must be carried out by all means, it may interfere with consultations.

<3> Using even an existing large-capacity magnetic disk drive or magneto-optical disk drive (automatic changer), it is impossible to store medical information of all patients and information of medical images thereof on a permanent basis. All data items are not always accessible.

<4> All medical institutions do not have similar hardware environments. Preparing equipment necessary for enabling any other medical institution to reference clinical recordings is too costly and hardly feasible.

<5> For improving the quality of medical care, it is more important that examination-related images, information of physical checkups, and biomedical information can be referenced in relation to a clinical recording than that examination-related images alone can be referenced. However, PACS does not provide a framework for an idea of handling medical information as multimedia data.

<6> The storage capacity of a card type storage medium is relatively small and the application range thereof is limited. Moreover, the precondition that clinical recordings should exist in each hospital must be satisfied.

As mentioned above, according to the known method, it is hard to materialize a wide-area hospital information system using a network such as the Internet as a medium.

SUMMARY OF THE INVENTION

The present invention attempts to break through the foregoing current situation. A major object of the present invention is to solve the problem of the storage capacity of a portable storage unit, and to provide an electronic clinical recording system for a wide-area hospital information system enabling the whole of a region to share medical information at low cost without any concern about a difference in type of equipment or OS.

A secondary object of the present invention is to at least make it possible to reference various clinical histories of a patient and records of consultations or medications the patient has received at another medical institutions during consultation of the patient, to view images in relation to a clinical recording, to copy basic personal information or information of allergies for saving the man power required for the work of creating a clinical recording, or to graphically display any data out of a consultation record for a patient's better understanding of diagnosis.

According to the gist of the present invention attempting to solve the aforesaid problems, a wide-area hospital information system is such that: an individual keeps a portable storage medium functioned as a clinical recording as a health care/medical care/welfare card (referred to as a patient card); when consulting at a medical institution, an individual presents his/her patient card; medical information is recorded in a patient card at the medical institution; and even when a patient visits another medical institution, his/ her past consultation records can be acquired and referenced remotely at the medical institution. For realizing this system, each consultation record including information of examinations, information of examination-related images, information of physical checkups, and biological information is described in SGML or HTML and contained in a data file. For storing the consultation record in the patient card, a specified group of files is not stored in the patient card, but link information is converted or produced so that the group of files can be referenced as external information, and then the consultation record is stored in the patient card. On the other hand, for reading a consultation record from the patient card and displaying it, the contents of an intended file are referenced according to link information, or an intended file is acquired on the basis of link information and the contents of the file are displayed together with or separately from the consultation record.

In order to realize the above objects, the system according to the present invention is constructed such that the system handling, as electronic data, information including a patient's consultation record, comprising: a portable storage medium for storing the patient's consultation record; means for writing the patient's consultation record described in a structured language into the storage medium; and means for reading the patient's consultation record from the storage medium. The writing means includes converting/producing means for converting or producing link information in the consultation record when the consultation record is written in the storage medium, the link information being indicative of making reference to a one or more specified files relevant to the consultation record and prepared as external information. The reading means includes data acquiring/referencing means for acquiring or referencing the one or more specified files indicated by the link information when the consultation record is read from the storage medium.

Preferably, the structured language is at least one of a SGML (Standard Generalized Markup Language) and an HTML (HyperText Markup Language). Still preferably, the storage medium is an IC card.

The operation of the electronic clinical recording system will be outlined below.

At the time of the first consultation, a reading means is used to read basic information of a patient from a patient card and a prototype of a consultation record is created. At this time, the name of a medical institution, a date on which the patient contracted the disease, and the name of a consulting physician are automatically registered and displayed. The patient's main complaint and the observed physical findings are then entered. If necessary, an order is placed for an examination or medication. Otherwise, while a treatment is undertaken, the contents of a therapy are entered.

If necessary, the results of past consultation records and periodical physical checkups are listed. The results of a consultation record and periodical physical checkup which may have relation are selected and displayed. At this time, if link information of the consultation record indicates external information, remote data is accessed according to the link information and acquired. A remote data acquiring/ referencing means is in practice the file transfer protocol (FTP), the protocol DICOM, a protocol for electronic mail, the hyper text transfer protocol (HTTP), or the protocol Telnet. When data is compressed and encrypted, a data extracting/decrypting means processes received data. As soon as processing is completed, resultant data is displayed together with or separately from the consultation record. A writing means is used to store consultation records in a patient card one by one or all at once. For entering and editing a consultation record, an SGML/HTML editor that is an editor conformable to the SGML or HTML is employed. Even when a consultation record is merely referenced, a date of reference and the name of an operator (physician) specified by an operator specifying means are automatically appended to and recorded in the consultation record. This makes it possible to prevent an incident such as leakage of personal information caused by impaired morals.

When a diagnostic ultrasound system, endoscope system, CT system, diagnostic X-ray system, or MR system is used to carry out an examination, information of the examination is entered in a consultation record. Information acquired by a diagnostic medical imaging modality in which produced examination-related images are stored is input so that produced medical images can be referenced directly in relation to the consultation record. Link information is then produced by a link information converting/producing means. The consultation record is updated and stored in the patient card.

Moreover, produced medical images may be printed on film, fetched into a computer using a film digitizer, and then put in a file. In this case, the link information converting/ producing means is used to produce link information facilitating access to the file as external information. A consultation record is then updated and stored in a patient card. Furthermore, a file containing medical images may be copied to a patient card. In this case, link information is produced in order to enable access to the file, and a consultation record is updated and recorded in the patient card. Whether a file containing medical images is stored in a patient card for reference or referenced as external information is determined with a file size according to one method and is determined with a file type according to the other method. Incidentally, a date of examination and the name of an operator (examining technician) identified using the operator specifying means are automatically appended to and recorded in a consultation record.

If a hemomanometer, electrocardiograph, or the like is used to acquire biomedical information, information of an examination is entered in a consultation record. Data is fetched from the measuring instrument directly into a computer or using a network as a medium, and put in a file. The link information converting/producing means is then used to produce link information facilitating referencing of the file in relation to the consultation record. The consultation record is then updated and stored in a patient card. Moreover, data output from the measuring instrument to paper or the like may be fetched into a computer using an image scanner and then put in a file. In this case, the link information converting/producing means is used to produce link information facilitating referencing of the file in relation to the consultation record. The consultation record is then updated and stored in the patient card. Furthermore, a data file of blood pressures and a data file of electrocardiograms may be copied to a patient card. In this case, link information used to reference the file in relation to a consultation record is produced, and the consultation record is updated and stored in the patient card. Whether a file of biomedical information is stored in a patient card for reference or referenced as an external information is determined with a file size according to one method or determined with a file type according to the other method. Incidentally, a date of examination and the name of an operator (nurse) identified using the operator specifying means are automatically stored in the consultation record.

At the time of the second or subsequent consultation, the reading means reads basic information of a patient from a patient card, and consultation records are listed. When a relevant record is selected, the previous consultation record is displayed. At this time, a date of update is recorded automatically. If the name of a consulting physician is different from the previous one, the name of the consulting physician is appended and recorded automatically. If link information indicates external reference, the remote data acquiring/referencing means is used to reference the contents of a file residing in another computer according to the link information. The file is acquired and displayed together with or separately from the consultation record. The remote data acquiring/referencing means is in practice the FTP, the protocol DICOM, a protocol for electronic mail, the HTTP, or the protocol Telnet. It is therefore unnecessary to learn in what way data is actually stored in the computer. When received, the data is handled as a file. The data may be contained in a file or database or stored in a memory in another computer. If acquired data is compressed or encrypted, a data compressing/expanding means or data encrypting/decrypting means is used to return the data to the original form. The resultant data is then displayed. The physician comprehensively evaluates the results of various examinations, and enters his/her findings and the name of a disease. The writing means is then used to store consultation records in a patient card one by one or all at once. For entering and editing a consultation record, an SGML/HTML editor is employed.

For a patient's better understanding of a consultation record, a data graphing means is employed. Information of physical checkups or biomedical information including blood pressures are converted into graphic data and then displayed. Moreover, the information may be output to a printer in compliance with a patient's demand.

DESCRIPTION OF THE PREFERRED EMBODIMENT

One embodiment of the present invention will be described in conjunction with the appended drawings.

Figure 1:
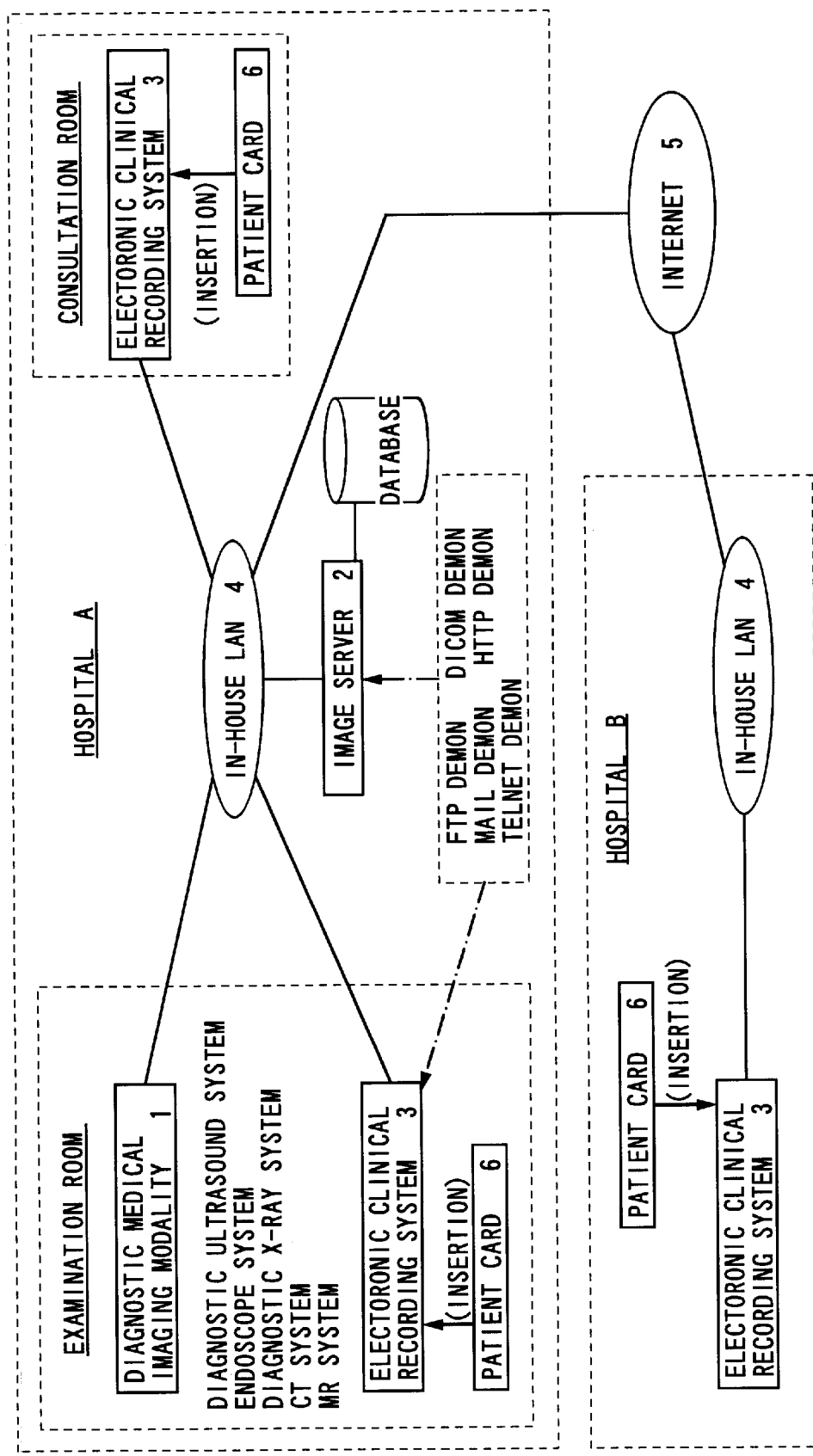
FIG. 1 shows one example of the configuration of a wide-area medical information system incorporating therein electric clinical recording systems to which the present invention is applied.

FIG. 1 shows the overview of a wide-area hospital information system in which an electronic clinical recording system of the present invention is included.

The illustrated wide-area hospital information system involves hospital A and hospital B. In one hospital A, a diagnostic medical imaging modality 1, an image server 2, and two electronic clinical recording systems 3 are interconnected on a local area network (LAN) 4 on the premises. In the other hospital B, an electronic clinical recording system 3 is connected on a local area network (LAN) 4 on the premises. The LANs 4 in hospitals A and B are linked to the Internet 5, whereby both the LANs can communicate with each other.

The diagnostic medical imaging modality 1 includes a diagnostic ultrasound system, endoscope system, diagnostic X-ray system, CT system, and MR system. The image server 2 is a computer system for managing information of medical images, and comprises a recording apparatus and a communication means enabling data transfer using the network as a medium. The recording apparatus may be a magneto-optical disk (MO) drive, hard disk drive (HDD), digital video disk (DVD) drive, or a portable disk (PD) drive. The electronic clinical recording system 3 starts operating with insertion of a patient card (health care, medical care, or welfare card) 6 serving as a clinical recording carried by a patient himself/herself.

For transferring data in response to a request made by the electronic clinical recording system 3 in hospital B, an FTP demon that is a demon conformable to the FTP, a DICOM demon that is a demon conformable to the protocol DICOM, a mail demon that is a demon conformable to a protocol for electronic mail, an HTTP demon that is a demon conformable to the HTTP, or a Telnet demon that is a demon conformable to the protocol Telnet, or a combination of them is running on the image server 2 and electronic clinical recording system 3 in hospital A. Images produced by the diagnostic medical imaging modality 1 are transferred to the image server 2 over the network or via an offline medium (for example, a magneto-optical disk).

Figure 2:
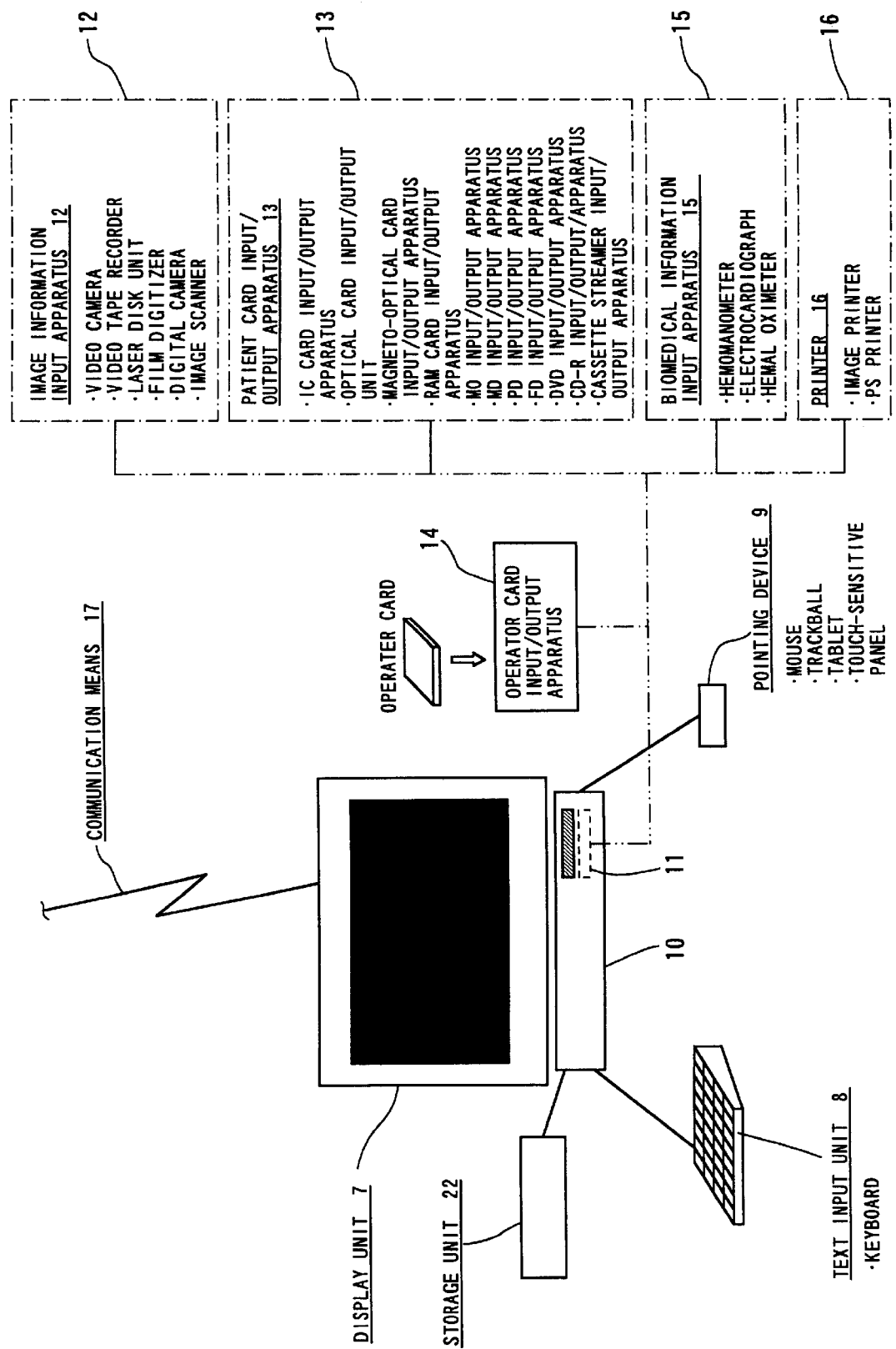
FIG. 2 shows one example of the configuration of one electric clinical recording system.

FIG. 2 shows a model of each electronic clinical recording system 3. The electronic clinical recording system 3 is an integral personal computer having a plurality of external equipment connected thereto. The personal computer may be of a tower type, a desktop type, or a notebook type or may be a workstation.

The electronic clinical recording system 3 includes a display unit 7, an input unit 8 used to enter information of a text, a pointing device 9, and a computer body 10.

The display unit 7 displays information of medical images represented by a still image, motion picture, and graphic information, and information of a text represented by characters and symbols. For the illustrated display unit 7, a CRT display is adopted. Alternatively, a liquid-crystal panel or television set will do. The input unit 8 is a keyboard enabling direct entry of characters, symbols, and programming data or enabling conversion of input characters into kana and kanji characters. The pointing device 9 is a mouse, trackball, touch-sensitive panel, or tablet. The computer body 10 is designed to control and manage the units and process data, and composed of a CPU, a memory, a storage unit 22, and others. The storage unit 22 is made by combining any of a magneto-optical (MO) disk drive, hard disk drive (HDD), digital video disk (DVD) drive, and portable disk (PD) drive.

An external equipment control unit 11 for controlling external equipment is incorporated in the electronic clinical recording system 3. The external equipment to be controlled by the computer body 10 includes an image information input apparatus 12, a patient card input/output apparatus 13 that is an integral part of the patient card reading/writing means, an operator card input apparatus 14 that is an integral part of the operator specifying means, a biomedical information input apparatus 15, and a printer 16.

As the image information input apparatus 12, a motion picture fetching apparatus or motion picture reproducing apparatus such as a video camera., video tape recorder, or laser disk unit, or a still image fetching apparatus such as a digital camera, image scanner, or film digitizer is used in combination with an associated interface card. As the patient card input/output apparatus 13, an IC card input/output apparatus, optical card input/output apparatus, magnetic card input/output apparatus, RAM card input/output apparatus, magneto-optical disk input/output apparatus, mini-disk (MD) input/output apparatus, portable disk input/output apparatus, floppy disk (FDD) input/output apparatus, cassette streamer input/output apparatus, digital video disk input/output apparatus, or CD-ROM input/output apparatus is used in combination with an associated interface card.

The operator card input unit 14 is a unit for reading identification information of an operator card which specifies an operator. The operator card is given to every person who may be requested to operate the electronic clinical recording system 3; such as, physicians, examining technicians, and nurses. Identification information of each individual including an ID number is stored in advance in the operator card. The electronic clinical recording system 3 is programmed not to operate unless the operator card is first inserted into the operator card input unit 14. Thus, security is guaranteed. The contents of data to be processed (entered and edited) by operating the electronic clinical recording system 3 are determined according to the qualification of an operator, for example, whether the operator is a physician or examining technician.

As the biomedical information input apparatus 15, a hemomanometer, electrocardiograph, or hemal oximeter is used in combination with an associated interface card. The printer 16 is an image printer or PostScript printer.

Moreover, the electronic clinical recording system 3 includes, in addition to the foregoing components, a communication means 17 through which the electronic clinical recording system 3 is connected on a wire or wireless LAN, the ISDN, a general public switched line, a cable television line, a leased line, or the like, and which enables data transfer using a network as a medium.

Furthermore, the electronic clinical recording system 3 includes various means functionally realized by running installed software packages. Those means include a link information converting/producing means 18 (See FIG. 9 to be referred to later) for converting or producing link information that enables reference to specified data, which is contained in a group of specified files out of files written in SGML or HTLM and various data files which constitute a consultation record, and which are not stored in a patient card, as external information; a remote data acquiring/referencing means 19 (See FIGS. 6 and 10 to 14 to be referred to later) that when a consultation record stored in a patient card is displayed, if link information indicates external information, acquires associated files according to the link information; a data encrypting/decrypting means 20 (See FIGS. 6 and 9 to be referred to later) for making data drifting on a network more safe; a data compressing/expanding means 21 (See FIGS. 6 and 9 to be referred to later) for reducing a load imposed on a network; and a data graphing means 23 (See FIG. 6 to be referred to later) enabling graphic display of data for a patient's better understanding of data of physical checkups and biomedical information.

The items of a consultation record are structured like the table below.

| Item | Contents |
| --- | --- |
| Basic information | ID, name, address, health insurance card No., sex, date of birth, occupation and habit |
| Emergency information | Blood type, history of side effects of medicines the patient has suffered, allergies |
| Information of clinical histories of family | Clinical histories of the father, mother, brothers, and sisters |
| Consultation record | Main complaint, physical findings, conditions and signs, name of the disease, name of the medical institution, date when the patient contracted the disease and date of update, name |

-continued

| Item | Contents |
| --- | --- |
| | of the physcan, result of diagnosis (importance and grounds), listing of problems, results of various examinations, radiological report, letter of introduction, contents of orders, therapeutic schedule and contents of the therapy, information of medications (date of prescription, frequency, names of medicines, usage, quantities of medicines or medications per day) |
| Information of screenings | Dates of screenings, kinds of screenings, data of various screenings |

Moreover, information listed below is entered at minimum as link information. The link information may be changed depending on a condition. For example, if a certain date has not passed, link information A is accessed. Otherwise, link information B is accessed. A means for accessing link information includes the protocols listed below, and an address is composed of data items listed below.

| Item of linking information | Contents |
| --- | --- |
| Accessing means | FTP, protocol DICOM, protocol for electronic mail, HTTP, protocol Telnet |
| Address | URL and port No., Internet address, port No., bus name, mail address. An identifier indicating a file format or encoding format shall be appended to the address without fail. The format indicated by the identifier includes the GNUPLOT, JPEG, GIF, MPEG, PPM, AU, WAV, and MJPEG. With the identifier, processing to be carried out after reception of data is determined uniquely. |

Figure 3:
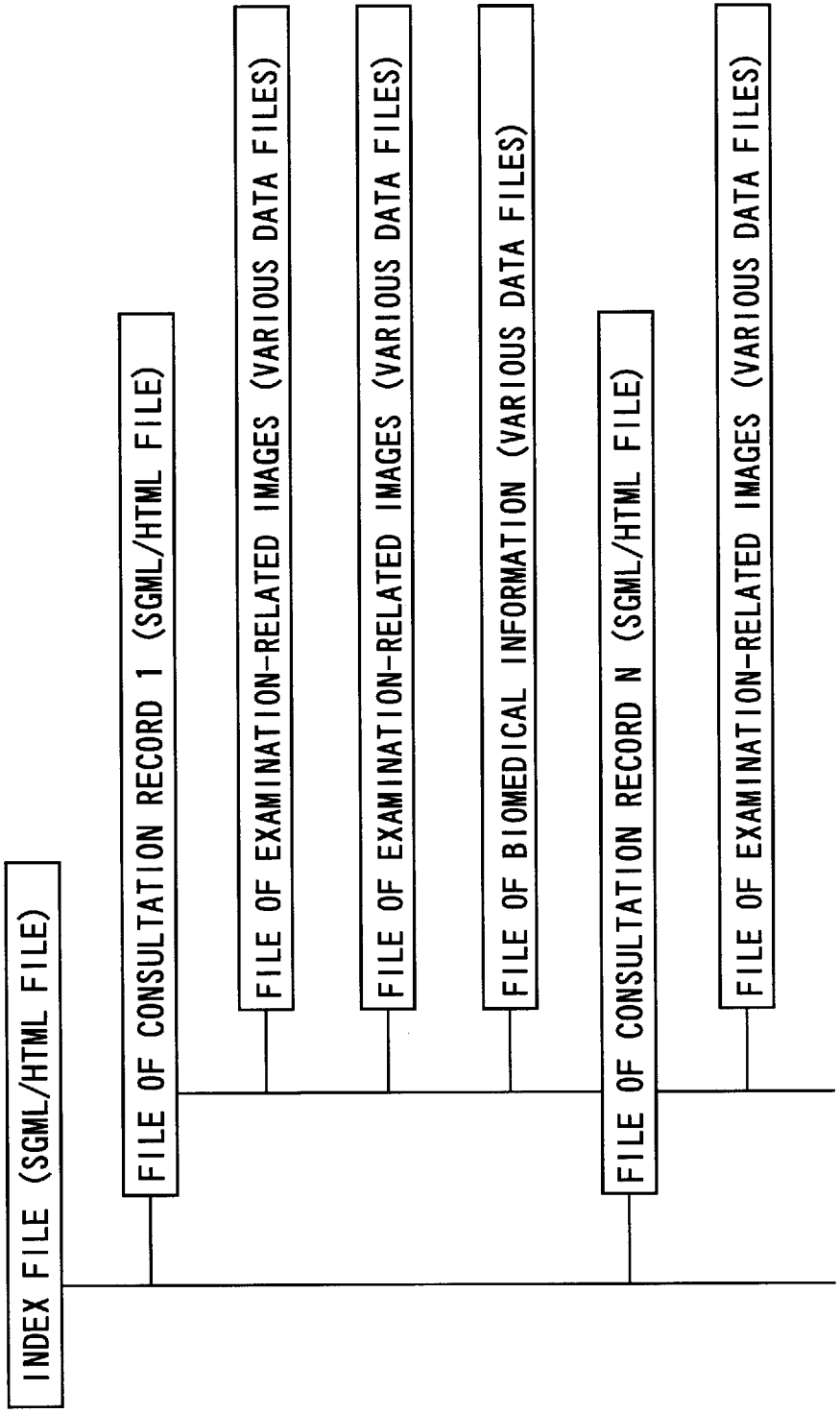
FIG. 3 shows one example of the file structure of a consultation record.
Figure 4:
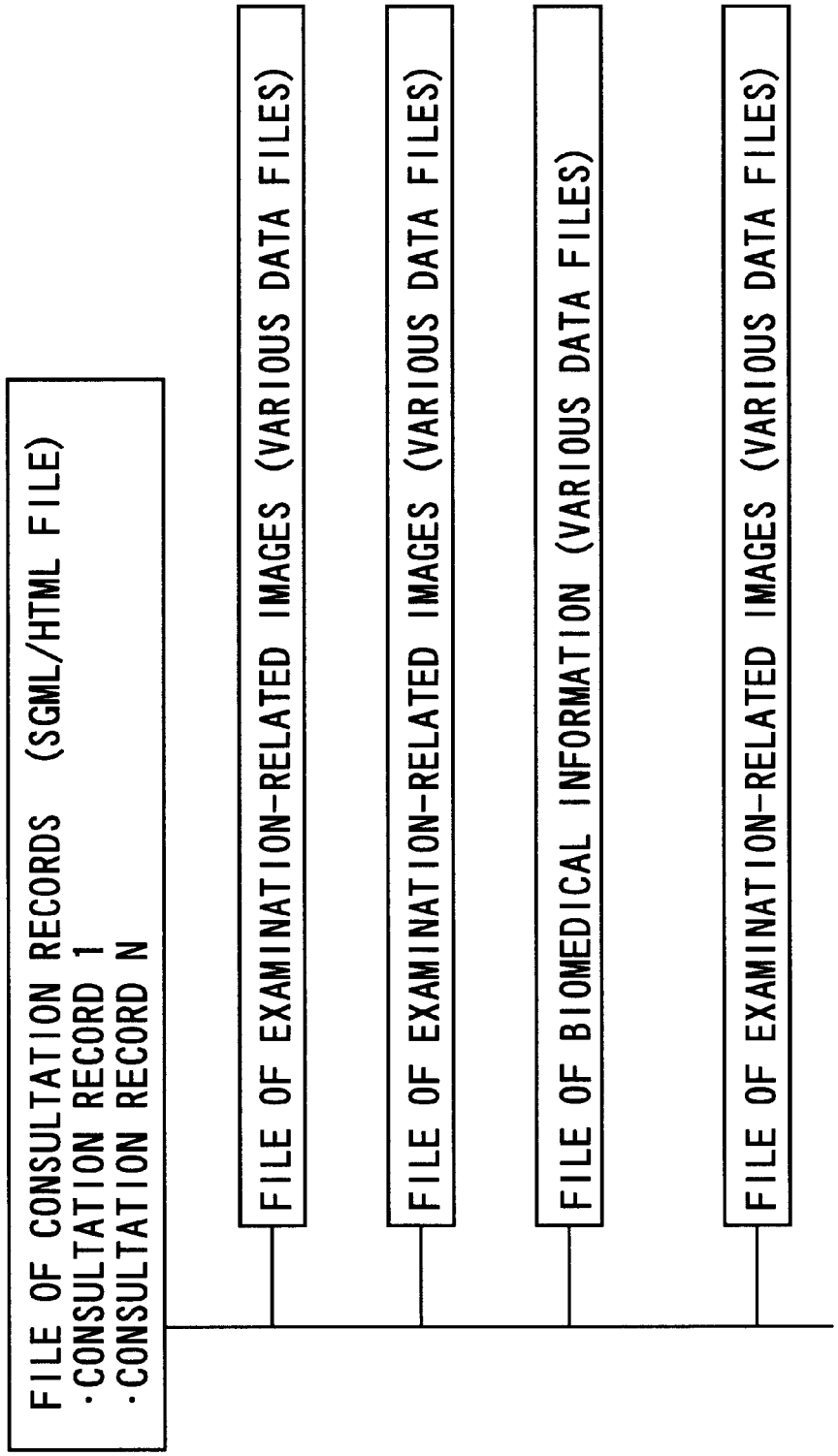
FIG. 4 shows another example of the file structure of a consultation record.

FIGS. 3 and 4 each show the data structure to consultation records. The consultation record is composed of a plurality of plain text files containing texts written in SGML or HTML, and a group of data files containing various data items. The HTML supports a description facilitating reference of an external file. Not only characters but also a still image, motion picture, voice, chart, and list can therefore be handled at the same time. Using a WWW browser, multimedia information can be viewed in a style that is the same among various models of computers or OSs. A specified WWW browser makes it possible to download a program written in Java or Visual Basic or a program written in JavaScript typical of a scripting language to the WWW browser, and to then execute the program.

In the example of the data structure of consultation records shown in FIG. 3, one consultation record is handled as an SGML/HTML file that is a file written in SGML or HTML, and one SGML/HTML file is prepared for an index facilitating reference of each consultation record. Within one consultation record, a plurality of different kinds of data files can be referenced if necessary. In the case of an IC card having a small storage capacity, the index file alone may be stored in the IC card.

In the example of the data structure of consultation records shown in FIG. 4, all consultation records are contained in one SGML/HTML file.

Figure 5:
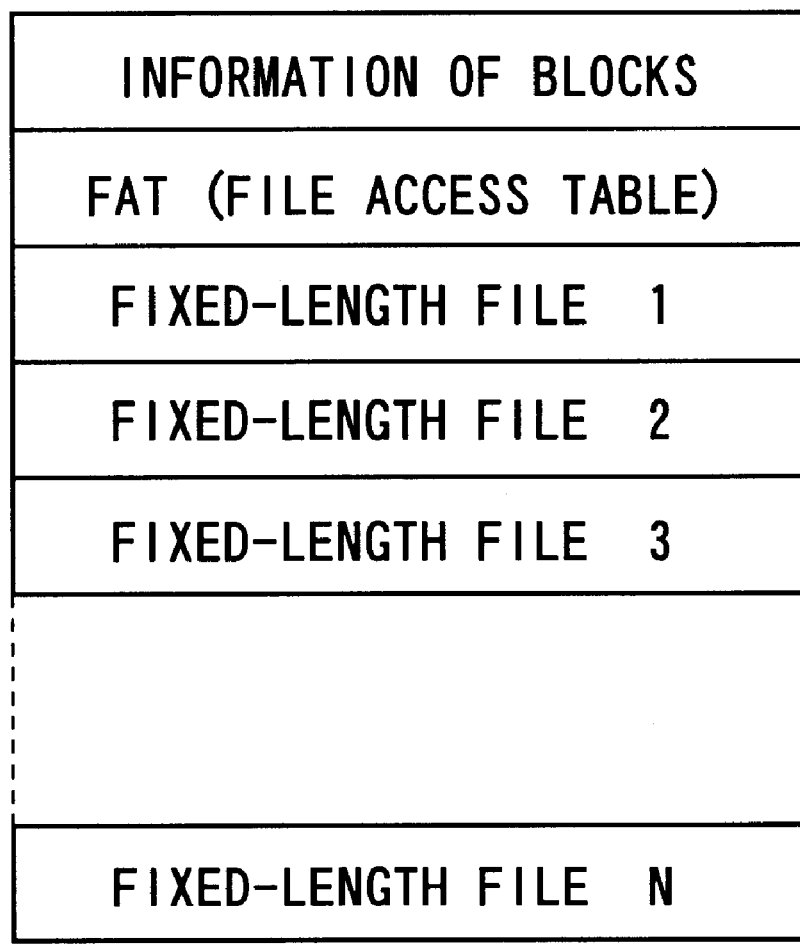
FIG. 5 exemplifies a data structure in the case of storing data in an IC card.

FIG. 5 shows an example of a recording format according to which consultation records are recorded on an IC card. The IC card can cope with fixed-length files alone. An available area file is created in the IC card. For storing a file whose size exceeds a pre-set size, overflowing data is automatically recorded in the available area file. There is therefore a case in which one logical file corresponds to a plurality of physical files. The logical and physical files as well as the relationship of correspondence between the logical and physical files are managed in the form of a file access table (FAT). In the case of the IC card, data input or output is carried out by way of a dedicated device driver.

By contrast, in the case of a CD-ROM, floppy disk, portable disk, mini-disk, or magneto-optical disk, files are used according to the DOS format that conforms to the ISO standards and is a de facto standard format and can be constructed as a file system. Moreover, in these disks, variable-length files can be stored as they are.

For an optical card, the format SIOC, format DELA, Olympus format, and others are presently available at. A data format stipulated in the ISO standards will be adopted. Even in the case of the optical card, data is input or output by way of a dedicated device driver.

Figure 6:
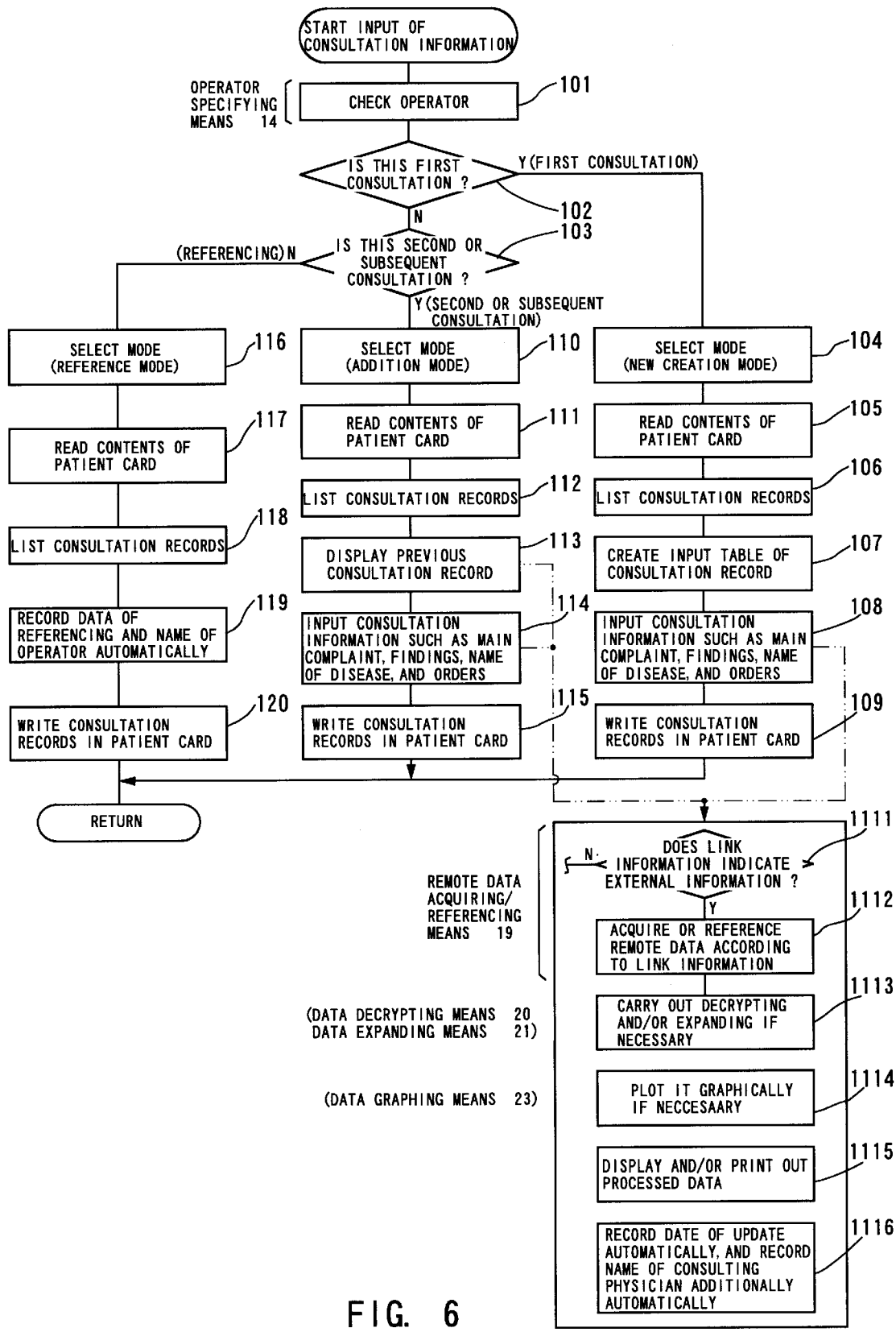
FIG. 6 is a flowchart explaining an outline of input processing of consultation information.
Figure 7:
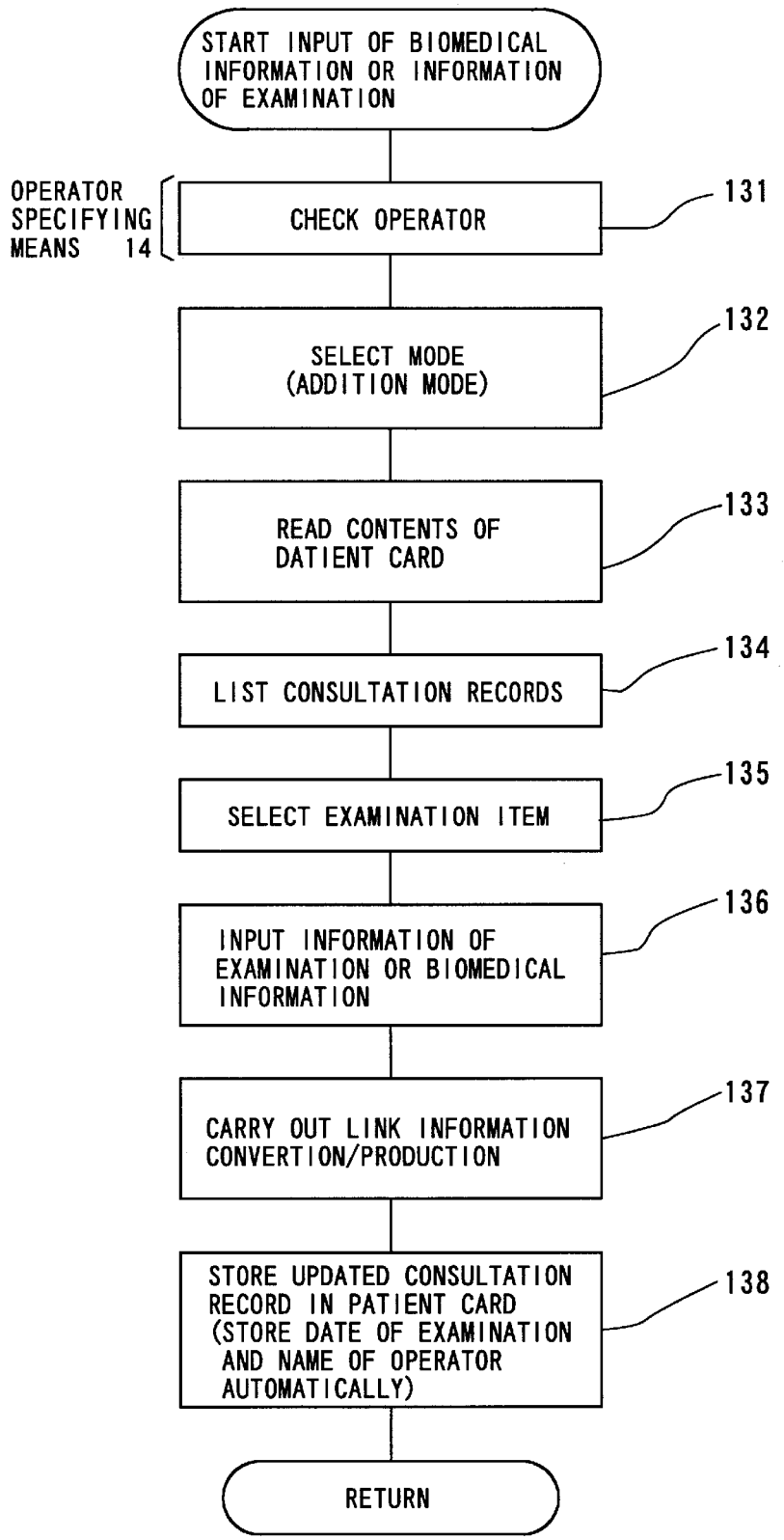
FIG. 7 is a flowchart explaining an outline of input processing of examination information and biomedical information.

After being activated, each electronic clinical recording system 3 can execute processing, which is outlined in FIGS. 6 or 7, by specifying a menu item. The processing described in FIG. 6 is carried out to assist a physician in entering consultation information into an electronic clinical recording (patient card 6). The processing described in FIG. 7 is carried out to assist an examining technician or nurse in entering information of examinations or biomedical information into the electronic clinical recording (patient card 6).

To begin with, the processing in FIG. 6 will be described. The electronic clinical recording system 3 reads information described in an operator card from the operator card input unit 14, and checks an operator and his/her qualification (step 101). With this check, an operator who has not had his/her name registered is excluded.

It is then judged from the input information sent from the input unit 8 or 9 whether or not this consultation is the first consultation or the second or subsequent consultation, or whether or not a consultation record is merely referenced (steps 102 and 103). If it is judged that this consultation is the first consultation, control is passed to a series of steps 104 to 109. If it is judged that this consultation is the second or subsequent consultation, control is passed to a series of steps 110 to 115. If it is judged that a consultation record is merely referenced, control is passed to a series of steps 116 to 120.

Figure 8:
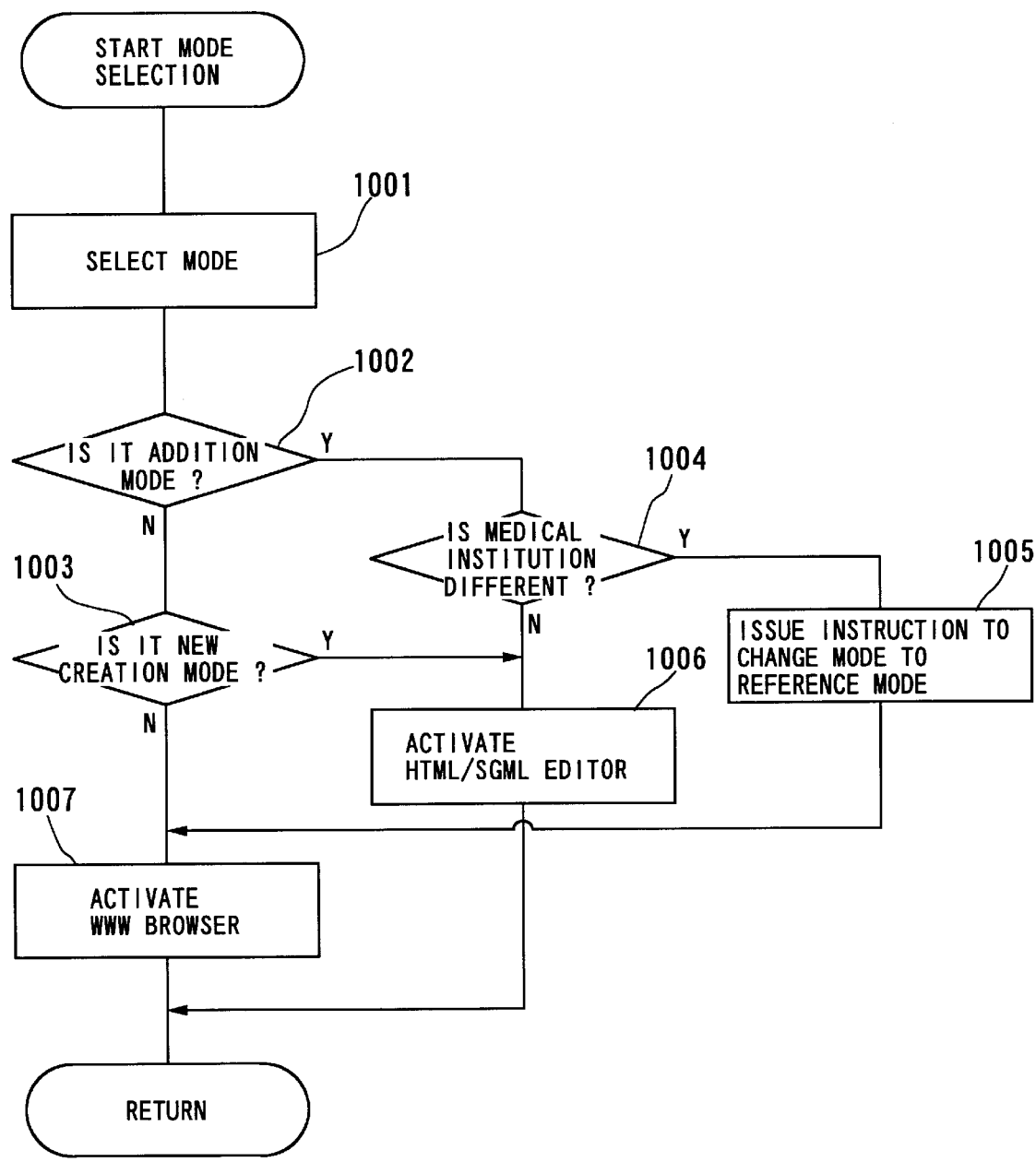
FIG. 8 is a flowchart showing the details of mode selection processing carried out in FIG. 6.

In the case of the first consultation, input mode selection is carried out first of all, and a new creation mode is thus set (step 104). The details of mode selection will be described in conjunction with the flowchart of FIG. 8. The electronic clinical recording system enables selection of any of three input modes. A job under way in the input mode can be displayed in a separate window in relation to a consultation record if necessary. The three modes are the new creation mode, an addition mode, and a reference mode.

The detailed mode selection at step 104 will now be described. At the electronic clinical recording system 8, an operator selects an input mode at step 1001 in FIG. 8. It is judged at step 1002 and 1003 whether the input mode is the addition mode, new creation mode, or reference mode. If the addition mode is selected, it is judged at step 1004 whether the name of a medical institution is different from the previous one. Even if the electronic clinical recording system 3 is activated in the addition mode, when the name of a medical institution is different from the previous one, the addition mode is automatically changed to the reference mode at step 1005. If the new creation mode or addition mode is selected, an HTML editor that is an editor conformable to the HTML or an SGML editor that is an editor conformable to the SGML is activated at step 1006. If the reference mode is selected, a WWW browser for interpreting and operating a Java applet is activated at step 1007.

When setting the new creating mode is completed, the electronic clinical recording system 3 reads the contents of the patient card 6 such as basic information via the patient card input/output apparatus 13, and lists them (steps 105 and 106 in FIG. 6). An input table of a consultation record is then created at step 107. At step 108, the main complaint of a patient, the findings of consultation, the name of a disease, and information of a consultation and treatment such as orders (information of a consultation) are input via the text input unit 8 and pointing device 9.

If necessary, external information can be acquired and referenced during the input. If link information indicating external information is contained in a consultation record, the external information is acquired and referenced remotely (steps 111 and 112) (Remote data acquisition will be described in conjunction with FIGS. 10 to 14). At this time, if remotely-acquired external data is encrypted, decrypting is carried out. If the external data is encrypted and/or compressed, expanding is carried out (step 1113). Moreover, given data included in the consultation record (for example, biomedical information such as blood pressures) is plotted graphically, and displayed on the monitor or printed out (steps 1114 and 1115).

When the above processing is completed, the consultation record is written in the patient card via the patient card input/output apparatus 13 and stored therein (step 109).

If the consultation is the second or subsequent consultation, the processing of steps 110 to 115 in FIG. 6 is executed sequentially. The electronic clinical recording system 3 carries out, as mentioned above, input mode selection and sets the addition mode (step 110). The details of mode selection are described in the above description of the flowchart of FIG. 8. The contents of a patient card are read and listed (steps 111 and 112). Thereafter, the consultation record of any previous consultation is displayed (step 113), and information of a present consultation is input (step 114). The updated consultation record is then written in the patient card and stored therein (step 115).

When the processing of step 113 is executed, a date of update is recorded automatically. When the name of a consulting physician is different from the previous one, the name of a consulting physician is automatically additionally recorded (step 116). The details of mode selection are described in the above description of the flowchart of FIG. 8. If referencing a consultation record is carried out in the addition mode but no data is added, the date of reference, the name of a referencing person, and the name of a referencing medical institution are automatically recorded.

When referencing alone is intended from the beginning, the processing of steps 116 to 120 is executed. That is to say, the electronic clinical recording system 3 selects an input mode (reference mode) (step 116), reads the contents of the patient card 6 (step 117), and lists consultation records (step 118). Referencing is then carried out. With the referencing, the date of referencing and the name of an operator are recorded automatically, and the consultation records are stored in the patient card 6 (steps 119 and 120).

Inputting information of an examination and biomedical information will be described in conjunction with FIG. 7.

The electronic clinical recording system 3 identifies an operator (step 131 in FIG. 7). Normally, when information of an examination such as medical images is input, the operator is an examining technician. In the case of biomedical information such as a blood pressure and electrocardiogram, the operator is usually a nurse. When the operator can be identified, the electronic clinical recording system 3 selects an input mode as mentioned above. In this case, the input mode is set to the addition mode (step 132).

The contents of the patient card 6 are then read and consultation records are listed (steps 133 and 134). Based on operational information input by handling, for example, the pointing device 9, an examination item (for example, an MR examination, or blood pressure examination) to which data is added is selected (step 135).

Thereafter, information of an examination or biomedical information is input (step 136). The input information is subjected to link information conversion/production (step 137) The link information conversion/production will be described with reference to FIG. 9. A consultation record to which the information of an examination or biomedical information is added is written and stored in the patient card 6 (step 138). Simultaneously with the storage, the date of an examination and the name of an operator are automatically stored.

Next, an algorithm used to carry out link information conversion/production described in FIG. 9 and executed by the electronic clinical recording system 3 will be described generally. When link information conversion/production is activated, the electronic clinical recording system 3 first inputs the attributes of data (for example, whether the data is image data or text data) (step 140). It is then judged whether or not data is input (step 141). For inputting data, the electronic clinical recording system 3 selects a device, reads data sent from the device, and puts the data in a file (steps 142 to 144). If the data has to be compressed, compression is carried out (steps 145 and 146). If the data has to be encrypted, encryption is carried out (steps 147 and 148).

The electronic clinical recording system 3 then selects a method for judging whether or not a specified file should be stored externally (step 149). There are two preferred methods, that is, a method based on a file size and a method based on a file type. It is then judged whether or not a file size is larger than a given size (step 150) or whether or not the file type is a file containing image data (step 151).

If the judgment determines that the file size is smaller and/or the data in a file is not image data, the file is copied to the patient card 6 (step 151). If it is determined that the file size is larger and/or the data in a file is image data, the file is copied to an external equipment such as the external image server 2 (step 152).

By contrast, if the judgment is made in the negative at step 141, that is, it is judged that no data is input, the processing of steps 142 to 152 is skipped.

Next, the electronic clinical recording system 3 judges whether or not a conditional statement instructing dynamic modification of link information is present (step 154). If the conditional statement is present, applet production and HTML statement production are carried out successively (steps 155 and 156). If the conditional statement is absent, HTML statement production alone is carried out (step 157). With the HTML statement production, link information is converted or produced.

Remote data acquisition will be described. FIGS. 10 to 14 show examples of implementing the remote data acquiring/referencing means 19.

Figure 10:
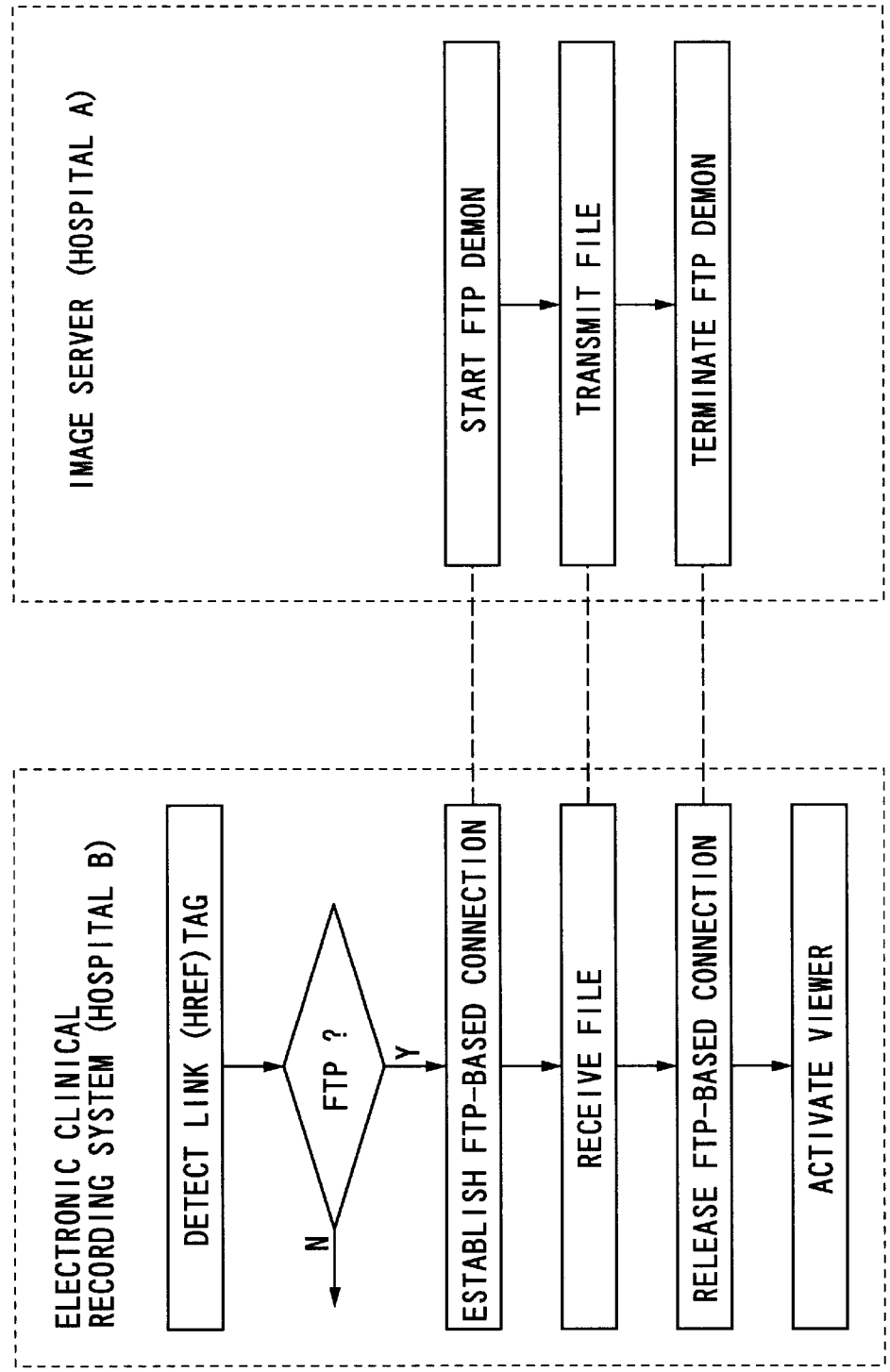
FIG. 10 is a flowchart representing an outline of acquisition of remote data on the FTP method.

FIG. 10 outlines a method in which the FTP is used as a protocol for data exchange. The description will proceed on the assumption that a consultation record produced at hospital A is displayed using the electronic clinical recording system at hospital B. In a consultation record, link information indicating that examination-related images are stored in the image server at hospital A shall be described as follows:

Exam.:<A HREF="ftp://www.hospitcal-A.co,jp/images/slice1.jpeg">MR exam.</A>

When the mouse button is clicked in "MR exam." within a WWW browser, the WWW browser requests the image server at hospital A to establish an FTP-based connection. The image server activates an INET demon that is a demon conformable to the protocol INET or the FTP demon so as to establish a communication connection. A User command or Pass command is transmitted and login is executed. A Binary command is then transmitted in order to change transfer modes. A Get command is then transmitted, thus asking transfer of a file "image/slice1.jpeg". Finally, a Quit command is transmitted in order to release the connection. Since the identifier of a received file name indicates images, an image viewer is activated in order to display the contents of the file. Thus, examination-related images in the image server at hospital A can be referenced.

Figure 11:
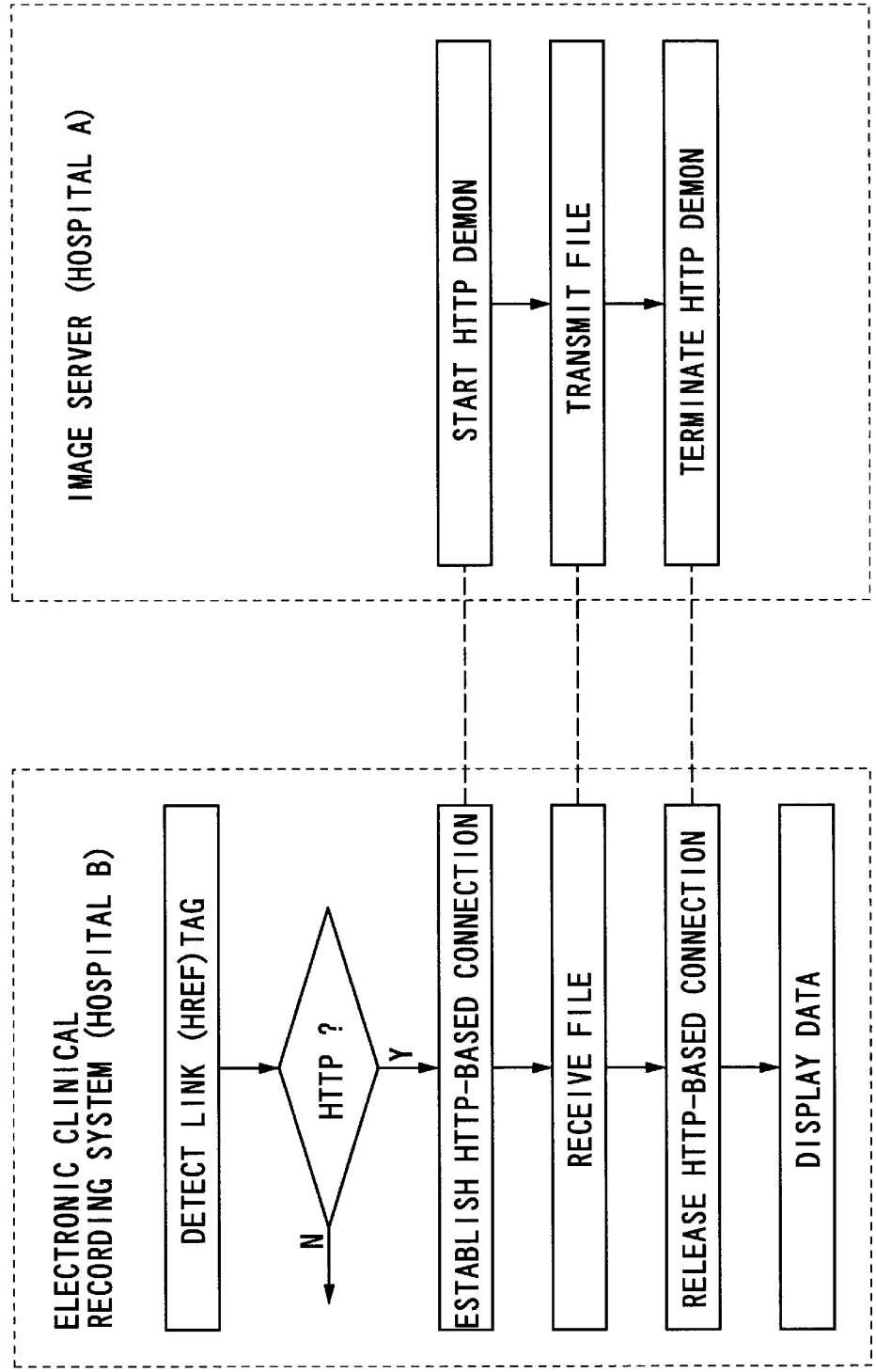
FIG. 11 is a flowchart representing an outline of acquisition of remote data on the HTTP method.

FIG. 11 outlines a method in which the HTTP is used as a protocol for data exchange. The description will proceed on the assumption that a consultation record produced at hospital A is displayed using the electronic clinical recording system at hospital B. In the consultation record, link information indicating that examination-related images are stored in the image server at hospital A shall be described as follows:

Exam.:<BR>
<IMG SRC="http://www.hospitcal-A.co.jp/images/slice1.jpet"WIDTH=256 HEIGHT=256>

For displaying the consultation record within a WWW browser, the WWW browser requests the image server at hospital A to establish an HTTP-based connection. The HTTP demon operating on the image server establishes a communication connection in response to the request. Transfer of a file "images/slice1.jpeg" is requested. After the transfer is completed, the connection is released. Since the identifier of the received file name indicates images, the images appear in a page, in which the consultation record is displayed, within the WWW browser. As a result, the examination-related images in the image server at hospital A can be referenced.

Figure 12:
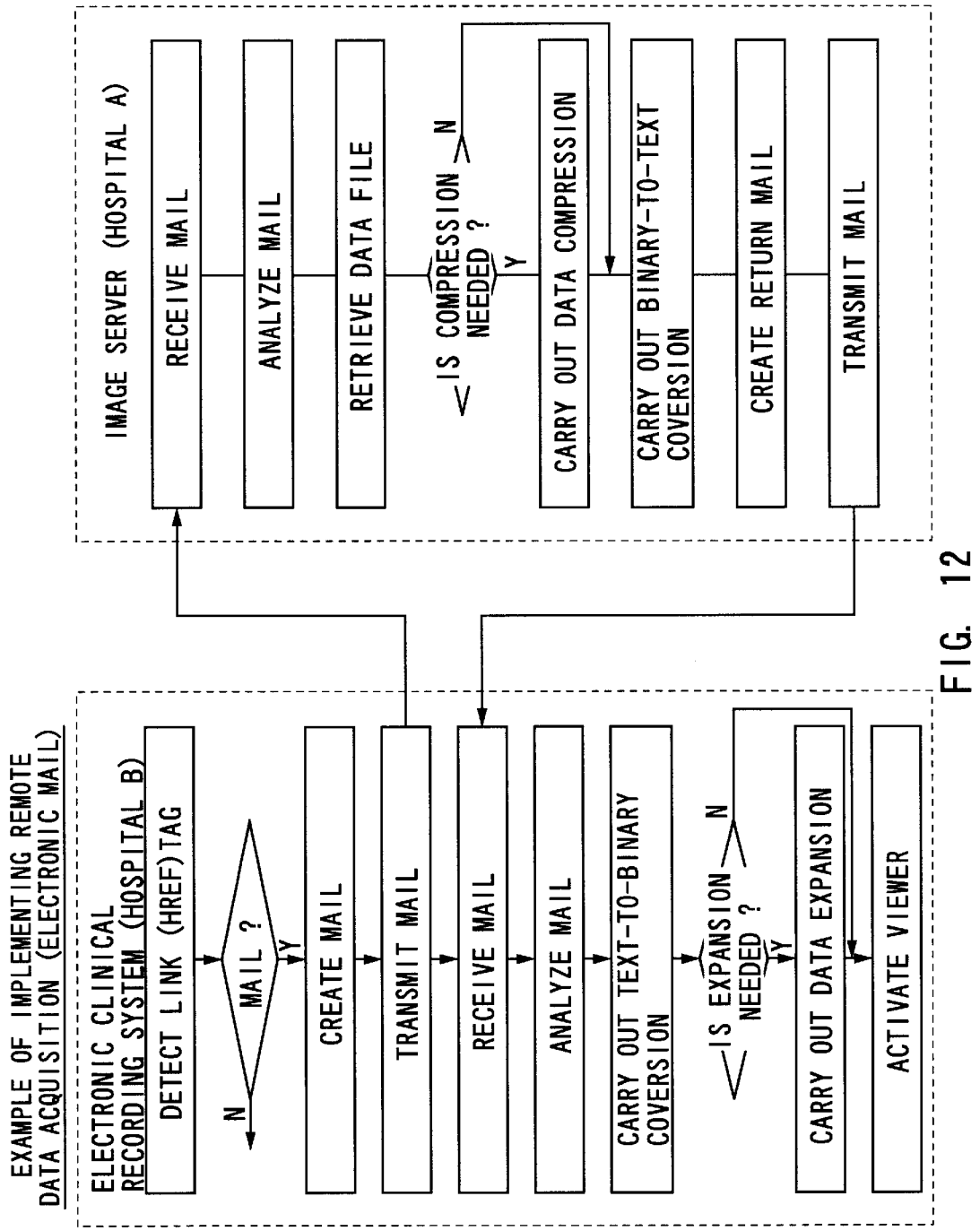
FIG. 12 is a flowchart representing an outline of acquisition of remote data on the electric-mail method.

FIG. 12 outlines a method in which a protocol for electronic mail is used as a protocol for data exchange. The description will proceed on the assumption that a consultation record produced at hospital A is displayed using the electronic clinical recording system at hospital B. In the consultation record, link information indicating that examination-related images are stored in the image server at hospital A shall be described as follows:

Exam.:<A HREF="mail-to:operator@hospitcal-A.co.jp">MR exam.</A>

When the mouse button is clicked in "MR exam." within a WWW browser, an electronic mail saying that a file "images/slice1.jpeg" is needed is created within the WWW browser and transmitted to an address "operator@hospital-A.co.jp." The electronic mail arrived at the image server in hospital A is detected by a program for checking the arrival of electronic mail which is activated periodically by a CRON demon that is a demon conformable to the protocol CRON. The contents of the mail are analyzed, and a return mail is transmitted with a text file into which a binary file "images/slice1.j.peg" is converted added thereto. Even in the electronic clinical recording system, the arrival of the electronic mail is detected, the contents of the mail are analyzed, and text-to-binary conversion is carried out. Since the identifier of the file indicates images, the image viewer is activated in order to display the examination-related images. Thus, the examination-related images in the image server at hospital A can be referenced.

When the position of "MR exam." on the WWW browser is clicked with the mouse button, an electronic statement indicative of an "images/slice1.jpeg" file is desired is made and transmitted from the WWW browser to the destination of "operator@hospitcal-A.co.jp". The electronic mail arrival at the image server of the hospital A is detected and analyzed in terms of its content by a program, which is booted up regularly by a CRON demon, for checking the arrival of the electronic mail. The "images/slice1.jpeg" file is binary/text-converted and added to a return mail, which will be transmitted. In the electronic clinical recording system, the electronic mail arrival likewise is detected, analyzed in terms of its content, and text/binary-converted. Since the extension of the file represents an image, an image viewer is booted up, and the examination image is displayed, which makes it possible to make reference to examination images in the image server of the hospital A.

Figure 13:
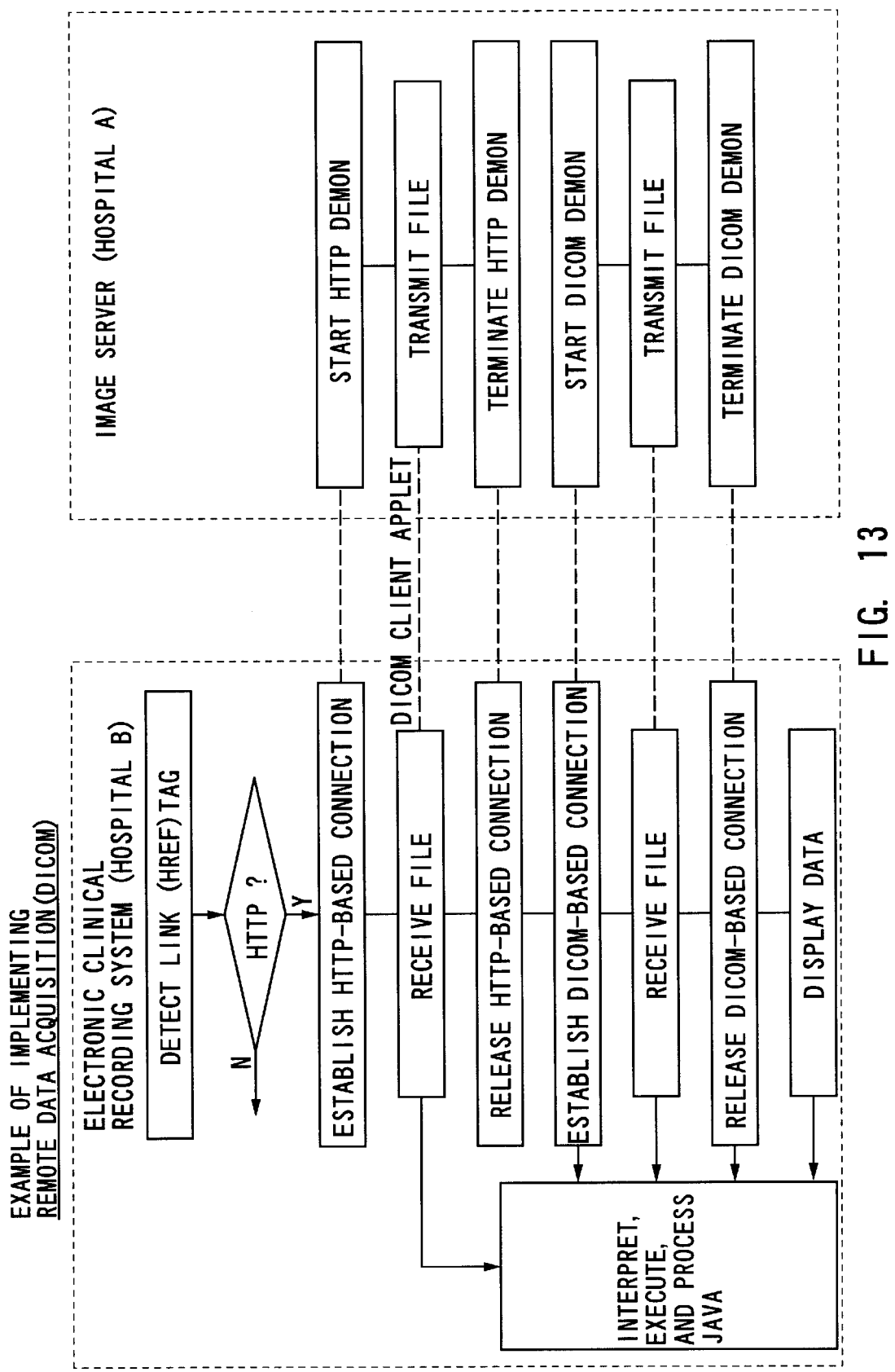
FIG. 13 is a flowchart representing an outline of acquisition of remote data on the DICOM method.

FIG. 13 shows the outline of a manner with which a DICOM is used as a protocol for transmitting and receiving data. This exemplifies a situation in which examined records preserved at the hospital A are displayed by the electronic clinical recording system of the hospital B. The consultation records are to include link information indicative of examination images stored in the image server of the hospital A, which is described as follows:

Exam.:<A HREF="http://www.hospitcal-A,co,jp/bin/dicom.html">MR exam.</A>

When the position of "MR exam." on the WWW browser is clicked with the mouse button, the WWW browser requests the establishment of a HTTP connection to the image server of the hospital A. The HTTP demon operating on the image server establishes the communication connection in response to the request. The demon receives not only a "bin/dicom.html" file but also a group of class files of the JAVA applet referred by the "bin/dicom.html" file, and then releases the communication connection. The JAVA applet has a DICOM client function and an image display function. In the "bin/dicom.html" file, an internet address of a computer to be connected, a port number, and information for identifying files to be transferred are described with PARAM tags. On the WWW browser, in the case of displaying HTML files, the JAVA applet is interpreted and performed, and a connection request is made to a DICOM demon operating in the image server of the hospital A. The DICOM demon establishes a communication connection in response to the request, and releaes the communication connection after reception of designated images. The JAVA applet depicts the received images on pages on which the consultation records are displayed. This permits reference to be made to the examination images stored in the image server of the hospital A.

Figure 14:
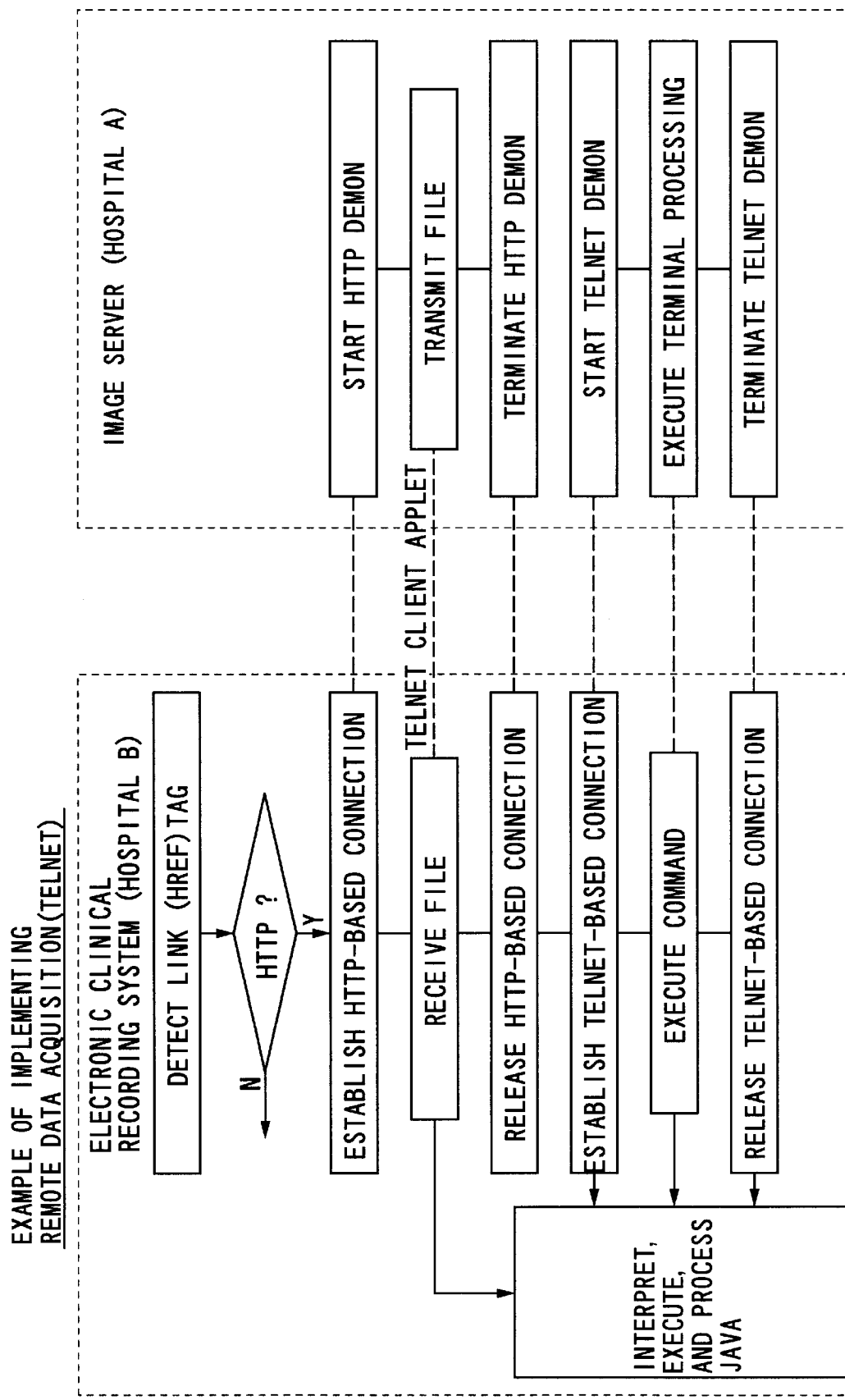
FIG. 14 is a flowchart representing an outline of acquisition of remote data on the TELNET method.

FIG. 14 shows the outline of a manner in which a TELNET is used as a protocol for making reference to data. This exemplifies a situation in which examined records preserved at the hospital A are displayed by the electronic clinical recording system of the hospital B. The consultation records include link information indicative of blood pressure data stored in the image server of the hospital A, which is described as follows:

Exam.:<A HREF="http://www.hospitcal-A,co,jp/bin/telnet.html">blood pressure data </A>

When the position of "blood pressure data" on the WWW browser is clicked with the mouse button, the WWW browser requests the establishment of a HTTP connection to the image server of the hospital A. The HTTP demon operating on the image server establishes the communication connection in response to the request. The demon receives not only a "bin/telnet.html" file but also a group of class files of the JAVA applet referred by the "bin/telnet.html" file, and then releases the communication connection. The JAVA applet has a TELNET client function. In the "telnet.html" file an internet address of a computer to be connected, a login name, a password, a command name for making reference to data, and file names to be referred are described with PARAM tags. On the WWW browser, in the case of displaying HTML files, the JAVA applet is interpreted and performed, and a connection request is made to a TELNET demon operating in the image server of the hospital A. The TELNET demon establishes a communication connection in response to the request, transmits a USER command and a PASS command, and carries out a login procedure. Subsequently, the demon performs a command making reference to designated files, and displays the performed results on pages on which the consultation records are displayed. And upon receiving an end request initiated from the user, the demon sends out a QUIT command to open the communication connection. This permits reference to be made to the blood pressure data stored in the image server of the hospital A.

In addition, procedures of data encrypting/decrypting, data compressing/expanding, and data graphing, executed according to necessities in the above various procedures, will now be described.

For performing data encrypting/decrypting, a wide range of manners possibilities are available, including a DES (Data Encryption Standard) which is the most widely used public key encryption. For example, in the case that software referred to as PGP (Pretty Good Privacy) is used as a means for encrypting/decrypting, individual public keys are first mutually exchanged between users who transmit and receive data. Then processing for encrypting is performed for a file to be transferred using public key information of itself, thereby an extension of "FILENAME .pgp" being added to the encrypted file. When the encrypted file is acquired through a medium such as a network, processing for decrypting is performed using the public key information which was used for the encrypting.

Methods of ZIP, COMPRESS, GNUZIP, PACK, and others are available for processing of data compressing/expanding. For example, when the COMPRESS method is used, an extension of "FILENAME.Z" is added to a compressed file. In this processing, a command "compress" is used for compressing, while a command "uncompress" is used for expanding.

For processing of data graphing, first, a specific key word is detected from the consultation records. Data files in association with the key words are then read for graphing them in time sequence. For example, HTML statements having words of "examination" and "blood pressure data" are expanded to not only detect file names and examination dates and times referred in the HTML statements but also read and data included in the files is realigned in the order of dates. Next, data of a two-dimensional graph is made from both the dates and blood pressure data in order to display them on the screen. Visualizing changes in states of a living body is useful in explaining the effects of treatment to a patient and her or his present condition.

Operators in charge of the electric clinical recording system 3 are previously registered. In specifying operators, there are a wide range of methods including a method of inputting login names and passwords, a method of reading operator ID cards, a method of inputting operator's fingerprints, and a method of specifying operator's faces through taking photographs thereof with cameras etc. This embodiment uses the method of reading operator ID cards.

Roles of the electric clinical recording system in the wide-area hospital information system shown in FIG. 1 will now be described in sequence.

(1) At a consultation room of the hospital A, a doctor first boots up the electric clinical recording system 3, and insert her or his ID card into the operator card input apparatus 14 employed as operator specifying means, thus the operator is identified. A patient card 6 possessed by the patient is inserted in the patient card input/output apparatus 13, and information stored in the patient card is read to display a list of the past consultation records. When the patient has come for the first medical care, the "new creation mode" is selected to form an input table of consultation records based on the basic information stored in the patient card. At this time, the name of a medical institution, the year and date of occurrence, and an examining doctor's name are automatically registered and displayed.

The doctor then inputs the patient's main complaint, his findings, treatment, further examinations, and medication dosage according to necessities and prescribed treatment. At the end of the examination, the consultation records are stored into the patient card at any time or as a batch job through the patient card input/output apparatus.

(2) Where examination using the diagnostic medical imaging modality 1 is carried out at an examination room of the hospital A, acquired image data are transferred from the modality 1 to the image server 2 through the in-house LAN 4 and are administered therein.

(3) An examiner boots up the electric clinical recording system 3 placed in an examination room and registers the operator by inserting the operator's card into the operator card input apparatus 14 regarded as operator specifying means. After the examination has been finished, the patient card 6 possessed by the patient is inserted in the patient card input/output apparatus 13, and information stored in the patient card is read to display a list of consultation records. The examiner then selects a consultation record which has been is to be added to. After this, the examiner sets the "addition mode" to input his or her examination information into the system 3 so as to be placed at the item representing treatment content.

Figure 9:
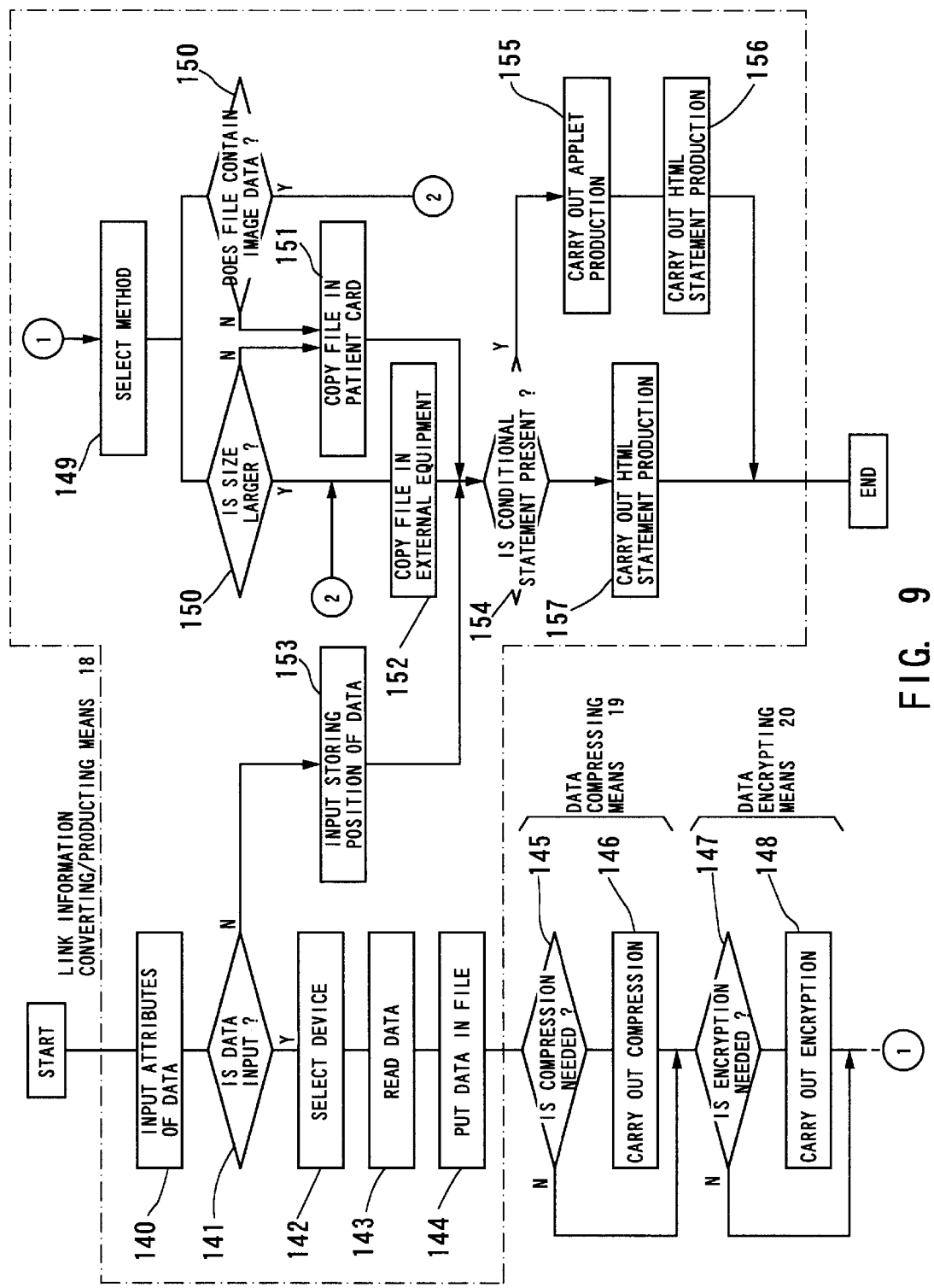
FIG. 9 is a flowchart representing an algorithm for the conversion/production of link information.

Next, through an algorithm for link information conversion/production means shown in FIG. 9, the examined image data registered into the consultation records is updated. In this case, since the image data themselves are stored in the image server 2, "no input data" is selected to input the internet address of the image server 2, a port number, an access method, image IDs, and others. Thus link information by which the examined images in the image server 2 can be referred from the consultation records is produced and the records are updated.

Link information to be used are changeable with changed conditions. One example is such that if "within 30 days from the examination date" is conditioned, the examined images are acquired using HTTP, while if "after 30 days from the examination date" is conditioned, the examined images are acquired using the E-mail. Such-conditions, which often occurs when exchangeable storage such as MODs or DVDs are used, result from the storage capacity of a image server incorporating such storage therein. In this case, selecting "condition exists" in the link information conversion/production means and inputting the conditions and alternative link information leads to a situation that a program written with the JAVA language is produced and converted into intermediate codes before an HTML file composing the consultation records so as to call the program are converted and produced. This permits the link information to be changed depending on given conditions.

When having completed the registration of the examined information, the updated consultation records are preserved in the patient card 6. The date of examination and the name of the operator (examining technician) recognized by the operator specifying means 14 are automatically preserved in the consultation records.

(4) In the diagnostic medical imaging modality 1, it is also possible that acquired medical images are printed on films and then processed by a computer before the images are preserved in a patient card. In FIG. 9 which represents an outline of an algorithm for a link information conversion/production means, first of all, "data input is required" is selected, a film digitizer is selected among the devices of the image information input apparatus 14, and the film is set on the digitizer to be read into the electric clinical recording system 3 and to be preserved in a file therein. Next, for compressing the data file, compressing/expanding means are used to perform compression. Likewise, for encrypting, encrypting/decrypting means are used for encrypting processing. For such processing, extensions are added to the file names so as to identify any necessary processing to return the data files to their original states and the order thereof. The link information is then converted or produced to be able to reference the data file from the consultation records, the records being thus updated.

There are two selectable methods concerning whether the data file is copied into the patient card 6 and link information to refer to them is created, or with the data file being not copied in the patient card, link information to refer to it, as external information, from the consultation records is produced. One method is defined according to the size of a file, whereas the other is defined according to the type of a file. Also, as described above, it is possible to alter link information to be used in conformity with given conditions. After having completed the registration of the examination information, the updated consultation records are preserved in the patient card 6, and the card is taken out. In the preservation into the patient card, the date of examination and the name of an operator (examining technician) recognized by the operator specifying means are automatically preserved in the consultation records.

For the sake of completeness it should be mentioned that the embodiment examples shown in the figures are not a definitive list of possible embodiments. The expert will appreciate that it is possible to combine the various construction details or to supplement or modify them by measures known from the prior art without departing from the basic inventive principle.

What is claimed is:

1. An electronic clinical recording system handling, as electronic data, information including a patient's consultation record, comprising:

a portable storage medium for storing the patient's consultation record described in a structured language as one or more specified files containing patient consultation information, as one or more of said specified files and link information indicating one or more external files containing patient consultation information, or as said link information;

means for writing said one or more specified files, said one or more specified files and link information or said link information at at least one of a plurality of medical institutions in order to initially store or to add to the patient's consultation record stored in the portable storage medium, said means for writing including converting/producing means for converting or producing the link information as part or all of the patient's consultation record when the patient consultation information is determined to have a predetermined characteristic; and means for reading the patient's consultation record from the portable storage medium at each of the plurality of medical institutions so that each medical institution can share the patient's consultation record, said means for reading further including data acquiring/referencing means for acquiring or referencing one or more external files indicated by any stored link information read from the portable storage medium, wherein the predetermined characteristic includes file size and the means for writing further includes first determining means for determining said file size of the one or more specified files and second determining means for determining whether or not to store the one or more specified files in the portable storage medium depending on the file size determined by the first determining means.

2. An electronic clinical recording system handling, as electronic data, information including a patient's consultation record, comprising:

a portable storage medium for storing the patient's consultation record described in a structured language as one or more specified files containing patient consultation information, as one or more of said specified files and link information indicating one or more external files containing patient consultation information, or as said link information;

means for writing said one or more specified files, said one or more specified files and link information or said link information at at least one of a plurality of medical institutions in order to initially store or to add to the patient's consultation record stored in the portable storage medium, said means for writing including converting/producing means for converting or producing the link information as part or all of the patient's consultation record when the patient consultation information is determined to have a predetermined characteristic; and means for reading the patient's consultation record from the portable storage medium at each of the plurality of medical institutions so that each medical institution can share the patient's consultation record, said means for reading further including data acquiring/referencing means for acquiring or referencing one or more external files indicated by any stored link information read from the portable storage medium, wherein the predetermined characteristic includes file type and the means for writing further includes first determining means for determining the file type of the one or more specified files and second determining means for determining whether or not to store the one or more specified files in the portable storage medium depending on the file type determined by the first determining means.

3. An electronic clinical recording system handling, as electronic data, information including a patient's consultation record, comprising:

a portable storage medium for storing the patient's consultation record described in a structured language as one or more specified files containing patient consultation information, as one or more of said specified files and link information indicating one or more external files containing patient consultation information, or as said link information;

means for writing said one or more specified files, said one or more specified files and link information or said link information at at least one of a plurality of medical institutions in order to initially store or to add to the patient's consultation record stored in the portable storage medium, said means for writing including converting/producing means for converting or producing the link information as part or all of the patient's consultation record when the patient consultation information is determined to have a predetermined characteristic; and means for reading the patient's consultation record from the portable storage medium at each of the plurality of medical institutions so that each medical institution can share the patient's consultation record, said means for reading further including data acquiring/referencing means for acquiring or referencing one or more external files indicated by any stored link information read from the portable storage medium, wherein the predetermined characteristic includes file type and file size and the means for writing further includes first determining means for determining the file type and the file size of the one or more specified files and second determining means for determining whether or not to store the one or more specified files in the portable storage medium depending on the file type and the file size determined by the first determining means.

4. An electrical clinical recording system handling, as electronic data, information including a patient's consultation record, comprising:

a portable storage medium for storing the patient's consultation record;

means for creating the patient's consultation record described in a structured language including determining means for determining that one or more patient consultation data files to be included in the patient's consultation record are of a particular file size or of a particular file type and means responsive to the determining means for enabling the creating means to create link information for accessing one or more external patient consultation data files instead of the actual patient consultation data files as at least a part of the created patient's consultation record and for otherwise creating the patient's consultation record so as to directly contain the one or more patient consultation data files;

means for writing the created patient's consultation record into the portable storage medium; and means for reading the patient's consultation record from the portable storage medium including means for acquiring or referencing the one or more external patient consultation data files indicated by link information when link information is read as part of the patient's consultation record.

5. An electronic clinical recording system handling, as electronic data, information including a patient's consultation record, the patient's consultation record being described in a structured language as one or more specified files containing patient consultation information, as one or more of said specified files and link information indicating one or more external files containing patient consultation information, or as said link information, the system comprising:

means for writing said one or more specified files, said one or more specified files and link information or said link information at at least one of a plurality of medical institutions in order to initially store or to add to the patient's consultation record, said means for writing including converting/producing means for converting or producing the link information as part or all of the patient's consultation record when the patient consultation information is determined to have a predetermined characteristic; and means for reading the patient's consultation record from storage at each of the plurality of medical institutions so that each medical institution can share the patient's consultation record, said means for reading further including data acquiring/referencing means for acquiring or referencing one or more external files indicated by any stored link information read as part of the patient's consultation record, wherein the predetermined characteristic includes file size and the means for writing further includes first determining means for determining said file size of the one or more specified files and second determining means for determining whether or not to store the one or more specified files as part of the patient's consultation record depending on the file size determined by the first determining means.

6. An electronic clinical recording system handling, as electronic data, information including a patient's consultation record, the patient's consultation record being described in a structured language as one or more specified files containing patient consultation information, as one or more of said specified files and link information indicating one or more external files containing patient consultation information, or as said link information, the system comprising:

means for writing said one or more specified files, said one or more specified files and link information or said link information at at least one of a plurality of medical institutions in order to initially store or to add to the patient's consultation record, said means for writing including converting/producing means for converting or producing the link information as part or all of the patient's consultation record when the patient consultation information is determined to have a predetermined characteristic; and means for reading the patient's consultation record from storage at each of the plurality of medical institutions so that each medical institution can share the patient's consultation record, said means for reading further including data acquiring/referencing means for acquiring or referencing one or more external files indicated by any stored link information read as part of the patient's consultation record, wherein the predetermined characteristic includes file type and the means for writing further includes first determining means for determining said file type of the one or more specified files and second determining means for determining whether or not to store the one or more specified files as part of the patient's consultation record depending on the file type determined by the first determining means.

7. An electronic clinical recording system handling, as electronic data, information including a patient's consultation record, the patient's consultation record being described in a structured language as one or more specified files containing patient consultation information, as one or more of said specified files and link information indicating one or more external files containing patient consultation information, or as said link information, the system comprising:

means for writing said one or more specified files, said one or more specified files and link information or said link information at at least one of a plurality of medical institutions in order to initially store or to add to the patient's consultation record, said means for writing including converting/producing means for converting or producing the link information as part or all of the patient's consultation record when the patient consultation information is determined to have a predetermined characteristic; and means for reading the patient's consultation record from storage at each of the plurality of medical institutions so that each medical institution can share the patient's consultation record, said means for reading further including data acquiring/referencing means for acquiring or referencing one or more external files indicated by any stored link information read as part of the patient's consultation record, wherein the predetermined characteristic includes file type and file size and the means for writing further includes first determining means for determining the file type and the file size of the one or more specified files and second determining means for determining whether or not to store the one or more specified files as part of the patient's consultation record depending on the file type and file size determined by the first determining means.

8. An electrical clinical recording system handling, as electronic data, information including a patient's consultation record, comprising:

means for creating the patient's consultation record described in a structured language including determining means for determining that one or more patient consultation data files to be included in the patient's consultation record are of a particular file size or of a particular file type and means responsive to the determining means for enabling the creating means to create link information for accessing one or more external patient consultation data files instead of the actual patient consultation data files as at least a part of the created patient's consultation record and for otherwise creating the patient's consultation record so as to directly contain the one or more patient consultation data files;

means for writing the created patient's consultation record into storage; and means for reading the patient's consultation record from storage including means for acquiring or referencing the one or more external patient consultation data files indicated by stored link information when link information is read as part of the patient's consultation record.

9. The system of claim 8, wherein the structured language is at least one of a SGML (Standard Generalized Markup Language) and an HTML (HyperText Markup Language).

10. The system of claim 8, wherein the storage of the created patient's consultation record by the writing means is into an IC card.

11. The system of claim 8, further including means for dynamically changing a content of the stored link information in a manner such that previously included acquiring or referencing information needed for the means for acquiring or referencing the one or more external patient consultation data files is changed according to the dynamically changed link information.

12. The system of claim 11, wherein the dynamically changing means includes means for writing a program into storage when the patient's consultation record is written into storage, said program being described in a programming language and containing instructions for dynamically changing the content of the stored link information under a prescribed condition or conditions.

13. The system of claim 8, further including means for dynamically changing a content of the stored link information in a manner such that the one or more external patient consultation data files previously designated for acquiring or referencing by the means for acquiring or referencing are eliminated and a new one or more external patient consultation data files are designated according to the dynamically changed link information.

14. The system of claim 13, wherein the dynamically changing means includes means for writing a program into storage when the patient's consultation record is written into storage, said program being described in a programming language and containing instructions for dynamically changing the content of the stored link information under a prescribed condition or conditions.

15. The system of claim 8, wherein the means for acquiring or referencing acquires or references the one or more patient consultation data files on the basis of at least one of protocols of an FTP (File Transfer Protocol), DICOM (Digital Imaging & Communication Medicine), electronic-mail, HTTP (Hyper Text Transfer Protocol), and TELNET (Telecommunication Network).

16. The system of claim 8, further comprising at least one of means for encrypting data contained in the one or more patient consultation data files and for decrypting the encrypted data and means for compressing data contained in the one or more patient consultation data files and for expanding the compressed data.

17. The system of claim 8, further comprising means for specifying an operator operating the system and means for restricting information to which the operator can obtain access depending on a result of specifying means.

18. The system of claim 8, wherein the means for reading further includes means for graphing at least one of examination data and biomedical data which are included in the patient's consultation record and means for outputting the data graph by the graphing means.

19. The system of claim 8 further comprising means for graphing at least one of examination data and biomedical data which are included in the patient's consultation record and means for outputting the data graph produced by the means for graphing.

20. The system of claim 8, wherein the means for reading further includes means for displaying data included in the patient's consultation record.

21. The system of claim 8, wherein said means for reading the stored patient's consultation record from storage is provided at each of the plurality of medical institutions so that each medical institution can share the patient's consultation record.

22. The system of claim 8, wherein the means for reading includes means for displaying data included in the patient's consultation record.

* * * * *